United States Patent [19]

Nesvadba

[11] Patent Number: 5,250,592
[45] Date of Patent: Oct. 5, 1993

[54] ISOINDOLINONE COMPOUNDS AS STABILIZERS FOR ORGANIC MATERIALS

[75] Inventor: Peter Nesvadba, Marly, Switzerland

[73] Assignee: Ciba-Geigy Corporation, Ardsley, N.Y.

[21] Appl. No.: 996,376

[22] Filed: Dec. 23, 1992

Related U.S. Application Data

[63] Continuation of Ser. No. 682,054, Apr. 8, 1991, abandoned.

[30] Foreign Application Priority Data

Apr. 12, 1990 [CH] Switzerland .................. 1283/90

[51] Int. Cl.$^5$ .............................. C08K 5/34
[52] U.S. Cl. ........................... 524/89; 524/83; 524/84; 524/133; 524/147; 252/51.5 R; 252/402; 252/403
[58] Field of Search ............... 524/83, 84, 89, 133, 524/147; 252/51.5 R, 402, 403

[56] References Cited

U.S. PATENT DOCUMENTS

| | | | |
|---|---|---|---|
| 2,860,985 | 11/1958 | Dann et al. | 96/109 |
| 3,507,867 | 4/1970 | Sulkowski et al. | 260/251 |
| 3,591,599 | 7/1971 | Hoehn et al. | 260/304 |
| 3,624,206 | 2/1971 | Milan et al. | 424/267 |
| 3,994,920 | 11/1976 | Sulkowskio | 424/244 |

FOREIGN PATENT DOCUMENTS

| | | |
|---|---|---|
| 1569613 | 6/1970 | Fed. Rep. of Germany . |
| 1670446 | 2/1971 | Fed. Rep. of Germany . |
| 2062022 | 7/1971 | Fed. Rep. of Germany . |
| 3230593 | 3/1983 | Fed. Rep. of Germany . |
| WO801566 | 2/1980 | PCT Int'l Appl. . |
| 887272 | 1/1962 | United Kingdom . |
| 1258351 | 12/1971 | United Kingdom . |

OTHER PUBLICATIONS

C. H. Gaozza et al., J. Het. Chem. 9, 883 (1972).
S. E. Piatti et al., Anal. Asoc. Quin. Arg., 70, 651 (1982) (English Abst).
Marck Index, No. 3829.
L. Somogyi, Liebigs Ann. Chem., 1985, 657 (English Abst).
P. Aeberli et al., J. Org. Chem. 34, 165 (1969).
A. Nakamura et al., Chem. Pharm. Bull., 20, 69 (1972).
A. Nakamura et al., Chem. Pharm. Bull., 22,2142 (1974).
A. Hassner et al., Tetrahedron Letters, 46, 4475 (1978).
E. Haslam, Tetrahedron, 36, 2409 (1980).

Primary Examiner—Kriellion S. Morgan
Attorney, Agent, or Firm—Luther A. R. Hall

[57] ABSTRACT

Compositions comprising an organic material liable to thermal, oxidative and/or actinic degradation and at least one compound of the formula (I)

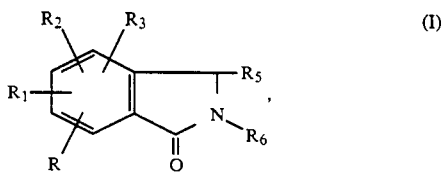

are described in which R is hydrogen, $C_1$-$C_{18}$alkyl, $C_1$-$C_{18}$alkoxy, halogen, nitro, phenyl-$C_1$-$C_4$alkoxy, $C_2$-$C_{18}$alkanoyl, benzoyl, ($C_1$-$C_6$alkyl)benzoyl, $C_2$-$C_{18}$alkenoyl, —N($R_7$)($R_{7a}$), —OH or —CO-A, $R_1$ has the same possibilities of meaning as R, $R_2$ is hydrogen or $C_1$-$C_4$alkyl and $R_3$ is hydrogen or halogen, A is hydroxyl, $C_1$-$C_{18}$alkoxy, $C_5$-$C_{12}$cycloalkoxy, benzyloxy or benzyloxy substituted by $C_1$-$C_4$alkyl and/or halogen, —N($R_7$)($R_{7a}$), —NH—NH—$R_8$ or leads to di-, tri- or tetrameric ring systems containing rings of the formula I via a bridging member, and in which $R_5$ and $R_6$ form the completion of a fused, substituted or unsubstituted, mononuclear to trinuclear ring system comprising at least one N, O or S atom as a ring member.

Some of these compounds are novel. They are particularly suitable for the stabilization of lubricating oils, metal processing fluids and hydraulic fluids, and of thermoplastics.

13 Claims, No Drawings

ISOINDOLINONE COMPOUNDS AS STABILIZERS FOR ORGANIC MATERIALS

This application is a continuation, of application Ser. No. 07/682,054, filed Apr. 8, 1991 now abandoned The present invention relates to compositions comprising an organic material liable to oxidative, thermal and/or actinic degradation and at least one isoindolinone compound. The invention further relates to the use of these compounds as additives for the stabilisation of organic material and to novel isoindolinone compounds.

2,3-Benzofuran and indolin-2-one compounds have already been proposed as stabilisers in polymeric organic materials (WO-A 80/01566). Nuclear (per)-chlorinated indolinone, isoindolinone and indolinedione compounds were mentioned in DE-A 3 230 593 as high pressure additives for lubricants. Certain isoindolinones were proposed as UV stabilisers in DE-A 1 770 439.

Isoindolinone compounds containing a further fused (hydro)pyridine ring were described in 1972 (C. H. Gaozza et al., J. Het. Chem. 9, 883 (1972)), to be precise with the aim of testing their pharmacological activity. Similar compounds were later also investigated for their suitability as DNA intercalators (S. E. Piatti et al. Anales Asoc. Quim. Argentina 70, 651 (1982)). Polycyclic, sulfur-containing compounds are additionally proposed in U.S. Pat. No. 3,591,599 as inflammation-inhibiting and analgesic agents which contain the isoindolinone ring system. Pharmaceutically active isoindolinone derivatives were also prepared the best-known of which is etomidoline, a spasmolytic (Merck Index, 10th ed., 3829, U.S. Pat. No. 3,624,206). The use of isoindolinone derivatives containing a fused (benzo)thiophene ring as fogging preventers in photographic silver halide emulsions is furthermore known (U.S. Pat. No. 2,860,985). In addition, a large number of documents are known which describe 8,9,10,11-tetrahydro-12-phthaloperinones as dye. As an example, see DE-A 1 569 613.

Other polycyclic compounds which contain a fused isoindole ring system have been investigated, for example, in the following literature references: Liebigs Ann. Chem. 1985, 657; J. Org. Chem. 34 (1969), 165; Chem. Pharm. Bull. 20 (1972), 69; Chem. Pharm. Bull. 22 (1974), 2142; U.S. Pat. No. 3,994,920; DE-A 1 670 446; U.S. Pat. No. 3,507,867; DE-A 2 062 022.

In the present application, isoindolinone compounds containing fused rings are now proposed for the first time in compositions containing organic materials to improve their stability and processibility.

Novel isoindolinone compounds have furthermore been found which are likewise excellently suited for the protection of organic material from thermal, oxidative and/or actinic degradation.

The present invention relates to compositions comprising an organic material liable to thermal, oxidative and/or cactinic degradation and at least one compound of the formula (I)

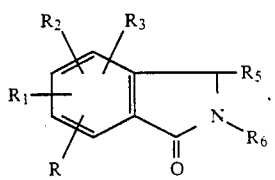

(I)

in which R is hydrogen, $C_1$-$C_{18}$alkyl, $C_1$-$C_{18}$alkoxy, halogen, nitro, phenyl-$C_1$-$C_4$alkoxy, $C_2$-$C_{18}$alkanoyl, benzoyl, ($C_1$-$C_6$alkyl)benzoyl, $C_2$-$C_{18}$alkenoyl, —N($R_7$)($R_{7a}$), —OH or —CO—A, $R_1$ has the same possibilities of meaning as R, $R_2$ is hydrogen or $C_1$-$C_4$alkyl and $R_3$ is hydrogen or halogen, A is hydroxyl, $C_1$-$C_{18}$alkoxy, $C_5$-$C_{12}$cycloalkoxy, benzyloxy or benzyloxy substituted by $C_1$-$C_4$alkyl and/or halogen, —N($R_7$)($R_{7a}$), —NH—NH—$R_8$ or —$G_1$—(G)$_n$, n is a number from 1 to 3 and G is radical of the formula

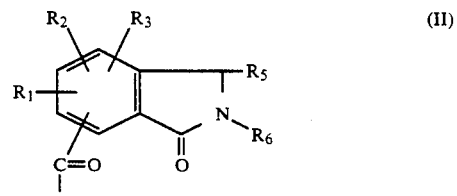

(II)

$G_1$ in the case where n=1 is —O—$R_{20}$—O—, —NH—$R_{21}$—NH— or —NH—NH—, in the case where n=2 is a group of the formula

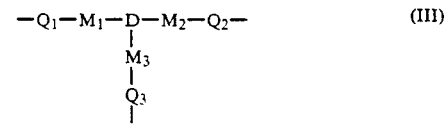

(III)

and in the case where n=3 is (—O—CH$_2$)$_4$C or

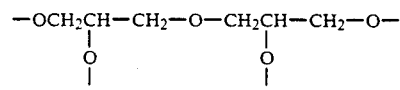

where D is N, CH or C($C_1$-$C_4$alkyl), $Q_1$, $Q_2$ and $Q_3$ independently of one another are O or NH and $M_1$, $M_2$ and $M_3$ independently of one another are $C_1$-$C_6$alkylene or $C_2$-$C_{12}$alkylene which is interrupted by —O—, or in the case where D=CH or C($C_1$-$C_4$alkyl) —M$_3$—Q$_3$ is also —O— or in the case where D=N —M$_3$—Q$_3$ is also a direct bond, $R_5$ and $R_6$ together form a group of the formula

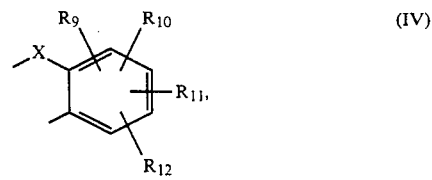

(IV)

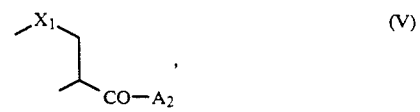

(V)

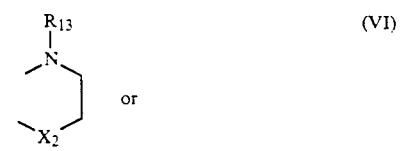

(VI)

or

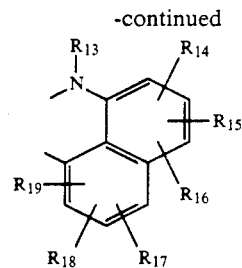

(VII)

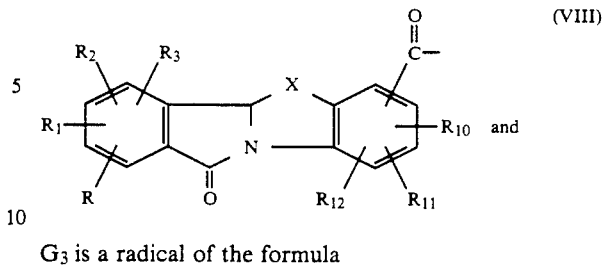

(VIII)

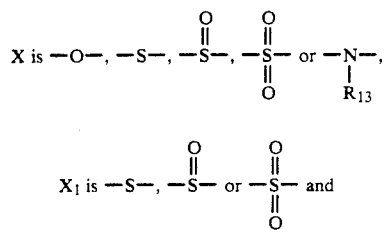

$G_3$ is a radical of the formula

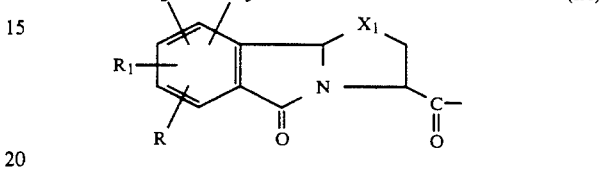

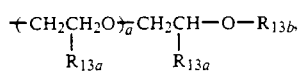

$X_2$ is —CH$_2$ or a direct bond, $R_7$ and $R_{7a}$ independently of one another are hydrogen, $C_1$-$C_{18}$alkyl, phenyl-$C_1$-$C_4$alkyl, $C_2$-$C_{18}$alkanoyl, $C_2$-$C_{18}$alkenoyl, $C_2$-$C_4$-hydroxyalkyl, benzoyl or ($C_1$-$C_6$alkyl)benzoyl or, together with the N atom to which they are bonded, are piperidyl, morpholinyl, piperazinyl or 4-methylpiperazinyl, $R_8$ is hydrogen, $C_2$-$C_{18}$alkanoyl, benzoyl or ($C_1$-$C_6$alkyl)benzoyl, $R_9$, $R_{10}$, $R_{11}$ and $R_{12}$ have the same possibilities of meaning as R, $R_1$, $R_2$ and $R_3$ (in this sequence), where —CO—A is to be replaced by —CO—A$_1$, $R_{13}$ is hydrogen, $C_1$-$C_{18}$alkyl, $C_2$-$C_{18}$alkenyl, $C_5$-$C_{12}$cycloalkyl, phenyl-$C_1$-$C_4$alkyl, $C_2$-$C_{18}$alkanoyl, $C_2$-$C_{18}$alkenoyl, benzoyl, ($C_1$-$C_6$alkyl)benzoyl, cyano-$C_1$-$C_4$alkyl, $C_2$-$C_{19}$alkoxycarbonyl-$C_1$-$C_4$alkyl, carboxy-$C_1$-$C_4$alkyl, hydroxy-$C_1$-$C_4$alkyl or $$\operatorname*{+\!\!\!\!\!\!\!\!\!\!\!\!\!\!\!\!\!\!\!\!\!\!\!\!\!}(CH_2CH_2O)_a^{} \underset{R_{13a}}{\overset{R_{13a}}{CH_2CH}}-O-R_{13b},$$

$R_{13a}$ is hydrogen or methyl and $R_{13b}$ is hydrogen, $C_1$-$C_{18}$alkyl, phenyl-$C_1$-$C_4$alkyl, $C_1$-$C_{18}$alkanoyl, benzoyl, $C_2$-$C_{18}$alkenoyl or ($C_1$-$C_6$alkyl)benzoyl and a is a number from 0 to 6, $R_{14}$, $R_{15}$, $R_{16}$, $R_{17}$, $R_{18}$ and $R_{19}$ independently of one another are hydrogen, $C_1$-$C_4$alkyl, halogen, hydroxyl, $C_1$-$C_{18}$alkoxy or —N($R_{7b}$)($R_{7c}$), in which $R_{7b}$ and $R_{7c}$ independently of one another are hydrogen or $C_1$-$C_{18}$alkyl, $R_{20}$ is $C_1$-$C_{12}$alkylene, $C_2$-$C_8$alkenylene, $C_3$-$C_6$alkynylene or $C_2$-$C_{24}$alkylene which is interrupted by O, S and/or —N($R_{22}$)—, $R_{21}$ is $C_1$-$C_{12}$alkylene and $R_{22}$ is hydrogen, $C_1$-$C_{18}$alkyl, phenyl, ($C_1$-$C_6$alkyl)phenyl or phenyl-$C_1$-$C_4$alkyl, $A_1$ is hydroxyl, $C_1$-$C_{24}$alkoxy, $C_5$-$C_{12}$cycloalkoxy, benzyloxy or benzyloxy substituted by $C_1$-$C_6$alkyl and/or halogen, —N($R_7$)($R_{7a}$), —NH—NH—$R_8$ or —G$_1$—(G$_2$)$_n$, and A$_2$ is hydroxyl, $C_1$-$C_{24}$alkoxy, $C_5$-$C_{12}$cycloalkoxy, benzyloxy or benzyloxy substituted by $C_1$-$C_6$alkyl and/or halogen, —N($R_7$)($R_{7a}$), —NH—NH—$R_8$ or —G$_1$—(G$_3$)$_n$, where G$_1$ and n are as defined above, G$_2$ is a radical of the formula with the proviso that only one substituent —CO—A, CO—A$_1$ or —CO—A$_2$ is present in the molecule, in which A, A$_1$ or A$_2$ is a radical —G$_1$—(G)$_n$, —G$_1$—(G$_2$)$_n$ or G$_1$—(G$_3$)$_n$.

If in the above formulae R, $R_1$, $R_9$, $R_{10}$, $R_7$, $R_{7a}$, $R_{7b}$, $R_{7c}$, $R_{13}$, $R_{13b}$ or $R_{22}$ are $C_1$-$C_{18}$alkyl radicals they are branched or unbranched. Examples of these are methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl; the radicals R, $R_1$, $R_2$, $R_7$, $R_{7a}$, $R_{7b}$, $R_{7c}$, $R_9$, $R_{10}$, $R_{13b}$ and $R_{22}$ in this case preferably have 1-12, in particular 1-4 C atoms. Possible $C_1$-$C_4$alkyl $R_2$ and $R_{14}$ to $R_{19}$ radicals are, for example, methyl, ethyl, propyl, isopropyl, n-butyl, isobutyl and t-butyl. Further alkyl groups in the above formulae which are not mentioned in more detail here have the same exemplary meanings.

Examples of $C_1$-$C_{18}$(or $C_1$-$C_{24}$)alkoxy groups R, $R_1$, $R_9$, $R_{10}$, A, $A_1$, $A_2$ and $R_{14}$-$R_{19}$ are derived from the radicals enumerated above for $C_1$-$C_{18}$alkyl groups plus eicosyl and docosyl as further examples and can be formally defined by appending the suffice -oxy.

If the substituents in formula I are halogen, these are to be understood as meaning, Cl, Br, F and I, in particular Cl and Br, especially Cl.

R, $R_1$, $R_7$, $R_{7a}$, $R_8$, $R_9$, $R_{10}$, $R_{13}$ and $R_{13b}$ as $C_2$-$C_{18}$alkanoyl are groups of the formula —CO—$C_1$-$C_{17}$alkyl. Examples of such radicals are obtainable by employing the radicals mentioned above for $C_1$-$C_{18}$alkyl (without octadecyl). $C_2$-$C_5$Alkanoyl is preferred for the radicals R, $R_1$, $R_9$ and $R_{10}$.

R, $R_1$, $R_9$ and $R_{10}$ as phenyl-$C_1$-$C_4$alkoxy is, for example, benzyloxy, phenethoxy, $\alpha$-methylbenzyloxy, or $\alpha,\alpha$-dimethylbenzyloxy. Benzyloxy is preferred. The same substituents and also $R_7$, $R_{7a}$, $R_8$, $R_{13}$ and $R_{13b}$ as ($C_1$-$C_6$alkyl)benzoyl can carry, for example, 1-3, especially 1 or 2, in particular 1 $C_1$-$C_6$alkyl group(s) in the phenyl radical. Examples of alkyl are mentioned further above. $C_1$-$C_4$Alkyl is preferred here, in particular methyl.

$R_{13}$ as $C_2$-$C_{18}$alkenyl can be branched or unbranched and is, for example, vinyl, allyl, 2-methallyl, hexenyl, undecenyl, heptadecenyl and oleyl.

R, $R_1$, $R_7$, $R_{7a}$, $R_9$, $R_{10}$, $R_{13}$ and $R_{13b}$ as $C_3$-$C_{18}$alkenoyl are radicals of the formula —CO—$C_2$-$C_{17}$alkenyl. Examples of such radicals are obtainable by employing the radicals mentioned above for $C_2$-$C_{18}$alkenyl (without oleyl).

$R_{13}$ as $C_5$-$C_{12}$cycloalkyl can be, for example, cyclopentyl, cyclohexyl, cycloheptyl, cyclooctyl or cyclododecyl. Cyclopentyl and cyclohexyl are preferred, in particular cyclohexyl.

$R_{13}$ as $C_2$-$C_{19}$alkoxycarbonyl-$C_1$-$C_4$alkyl is in particular $C_2$-$C_{19}$alkyloxycarbonylmethyl. The alkoxy moiety preferably has 1 to 12 C atoms.

Cycloalkoxy as a substituent A, $A_1$ or $A_2$ is, for example, cyclopentyloxy, cyclohexyloxy, cyclooctyloxy, cycloheptyloxy or cyclododecyloxy, cyclopentyloxy and in particular cyclohexyloxy being preferred.

Substituted benzyloxy as a substituent A, $A_1$ or $A_2$ contains, for example, 1 to 3 substituents from the series comprising halogen (in particular chlorine) and $C_1$-$C_6$alkyl. Either halogen or alkyl are preferably present as substituents. 1 or 2, especially 1 substituent, is expedient. Alkyl is especially $C_1$-$C_4$alkyl, in particular methyl.

$C_1$-$C_6$Alkylene (substituents $M_1$, $M_2$, $M_3$) and $C_1$-$C_{12}$alkylene ($R_{20}$, $R_{21}$) can be straight-chain or branched and is, for example, methylene, ethylene, propylene, butylene or hexylene and for $R_{20}$ and $R_{21}$ is additionally octylene, decylene and dodecylene, straight-chain radicals being preferred.

$R_{20}$ as $C_2$-$C_8$alkenylene or $C_3$-$C_6$alkynylene is, for example, vinylene, butenylene, hexenylene and octenylene or butynylene.

Examples of $C_2$-$C_{12}$alkylene ($M_1$, $M_2$, $M_3$) and $C_2$-$C_{24}$alkylene ($R_{20}$) interrupted by —O— are, for example, methoxyethyl, ethoxyethyl, butoxyethyl, butoxypropyl, —$CH_2OCH_2CH_2OCH_2CH_2$—, —$CH_2CH_2OCH_2CH_2$—, —$CH(CH_3)CH_2OCH_2CH(CH_3)$—, —$CH_2CH_2$—$OCH_2CH_2)_n$ where n=1 to 5 (for $M_1$, $M_2$, $M_3$) or 1 to 11 (for $R_{20}$).

Examples of $R_{20}$ as $C_2$-$C_{24}$alkylene interrupted by —S— or —N($R_{22}$)— are methylthiaethylene, ethylthiapropylene, octylthiapropylene or —$CH_2CH_2NHC_4H_8$—, —$(CH_2)_3NHC_8H_{16}$—, —$CH_2)_3N(CH_3)CH_2CH(C_2H_5)C_4H_8$—.

$R_7$, $R_{7a}$, $R_{13}$, $R_{13b}$ and $R_{22}$ as phenyl-$C_1$-$C_4$alkyl are, for example, benzyl, phenethyl, 3-phenylpropyl, α-methylbenzyl or α,α-dimethylbenzyl. Benzyl is preferred.

$C_2$-$C_4$Hydroxyalkyl as substituents $R_7$, $R_{7a}$ and $R_{13}$ contains, for example, 1 to 4 OH groups, for example 1-2, in particular 1 OH group. 2-Hydroxyethyl is preferred.

$R_{22}$ as ($C_1$-$C_6$alkyl)phenyl contains, for example, 1-3, especially 1 or 2, in particular 1 alkyl group (preferably having 1 to 4 C atoms, in particular methyl) on the phenyl radical. Examples are tolyl, dimethylphenyl, trimethylphenyl, t-butylphenyl and di-t-butylphenyl.

Examples of groups of the formula

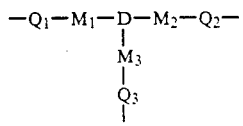

are the following: $N(CH_2CH_2O—)_3$, $CH_3C(CH_2O—)_3$, $CH_3CH_2C(CH_2O—)_3$,

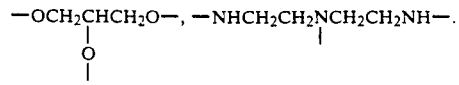

R and $R_1$ or $R_9$ and $R_{10}$ are expediently hydrogen, hydroxyl, $C_1$-$C_4$alkyl, chlorine, $C_1$-$C_4$alkoxy, benzoyl, $N(R_7)(R_{7a})$ or —CO—A, where $R_7$ and $R_{7a}$ are expediently hydrogen, $C_1$-$C_6$alkyl, benzyl, $C_2$-$C_4$hydroxyalkyl or, together with the N-atom to which they are bonded, are piperidyl, morpholinyl, piperazinyl or 4-methylpiperazinyl. Advantageous compounds containing the radical —CO—A as R or $R_1$ are those in which A is hydroxyl, $C_1$-$C_{18}$alkoxy, $C_5$-$C_6$cycloalkoxy, benzyloxy or benzyloxy substituted by $C_1$-$C_4$alkyl and/or chlorine or $N(R_7)(R_{7a})$. $R_2$ and $R_3$ or $R_{11}$ and $R_{12}$ are preferably hydrogen. At most one of the radicals R, $R_1$, $R_2$ and $R_3$ or $R_9$, $R_{10}$, $R_{11}$ and $R_{12}$ is particularly preferably different from hydrogen and is then in particular hydroxyl, $C_1$-$C_4$alkyl, chlorine or $C_1$-$C_4$alkoxy.

Of particular interest are compositions according to the invention comprising compounds of the formula I in which R is hydrogen, hydroxyl, $C_1$-$C_4$alkyl, chlorine, nitro, $C_1$-$C_4$alkoxy, benzoyl, —$N(R_7)(R_{7a})$ or —CO—A, $R_1$ has the same possibilities of meaning as R, $R_2$ is hydrogen or $C_1$-$C_4$alkyl and $R_3$ is hydrogen or chlorine, A is hydroxyl, $C_1$-$C_{18}$alkoxy, $C_5$-$C_6$cycloalkoxy, benzyloxy or benzyloxy substituted by $C_1$-$C_4$alkyl and/or chlorine, —$N(R_7)(R_{7a})$ or —$G_1$—$(G)_n$, n is a number from 1 to 3 and G is a radical of the formula

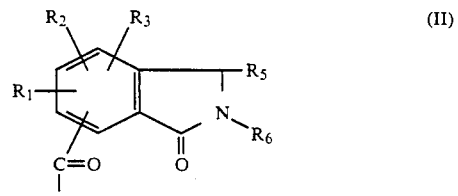

$G_1$ in the case where n=1 is —O—$R_{20}$—O— or —NH—$R_{21}$—NH—, in the case where n=2 is a group of the formula

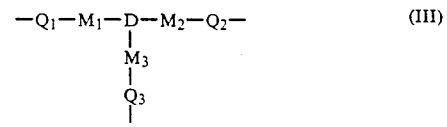

and in the case where n=3 is (—$OCH_2)_4C$, where D is equal to N, CH or C($C_1$-$C_4$alkyl), $Q_1$, $Q_2$ and $Q_3$ independently of one another are O or NH and $M_1$, $M_2$ and $M_3$ independently of one another are $C_1$-$C_6$alkylene or $C_2$-$C_{12}$alkylene interrupted by —O—, or in the case where D=CH or C($C_1$-$C_4$alkyl)—$M_3$—$Q_3$ is also —O— or in the case where D=N—$M_3$—$Q_3$ is also a direct bond, $R_5$ and $R_6$ together form a group of the formula IV, V, VI or VII, $R_7$ and $R_{7a}$ independently of one another are hydrogen, $C_1$-$C_6$alkyl, benzyl, $C_2$-$C_4$hydroxyalkyl or, together with the N atom to which they are bonded, are piperidyl, morpholinyl, piperazinyl or 4-methylpiperazinyl, $R_9$, $R_{10}$, $R_{11}$ and $R_{12}$ have the same possibilities of meaning as R, $R_1$, $R_2$ and $R_3$ (in this sequence), where —CO—A is to be replaced by —CO—$A_1$, $R_{13}$ is hydrogen, $C_1$-$C_{18}$alkyl, $C_2$-$C_{18}$alkenyl, $C_5$-$C_6$cycloalkyl, phenyl-$C_1$-$C_4$alkyl, $C_2$-$C_{18}$alkanoyl, $C_2$-$C_{18}$alkenoyl, benzoyl, ($C_1$-$C_6$alkyl)benzoyl, $C_2$-$C_{19}$alkoxycarbonyl-$C_1$-$C_4$alkyl, carboxy-$C_1$-$C_4$alkyl, cyano-$C_1$-$C_4$alkyl or hydroxy-$C_2$-$C_4$alkyl, $R_{14}$, $R_{15}$, $R_{16}$, $R_{17}$, $R_{18}$ and $R_{19}$ independently of one another are hydrogen, $C_1$-$C_4$alkyl, chlorine, hydroxyl, $C_1$-$C_4$alkoxy or —$N(R_{7b})(R_{7c})$, in which $R_{7b}$ and $R_{7c}$ independently of one another are hydrogen or $C_1$-$C_6$alkyl, $R_{20}$ is $C_1$-$C_{12}$alkylene, $C_2$-$C_8$alkenylene, $C_3$-$C_6$alkynylene or $C_2$-$C_{24}$alkylene interrupted by O, S and/or —$N(R_{22})$, $R_{21}$ is $C_1$-$C_{12}$alkylene and $R_{22}$ is hydrogen or $C_1$-$C_4$alkyl, $A_1$ is hydroxyl, $C_1$-$C_{18}$alkoxy, $C_5$-$C_6$cycloalkoxy, benzyloxy or benzyloxy substituted by $C_1$-$C_4$alkyl and/or halogen, —$N(R_7)(R_{7a})$ or —$G_1$—$(G_2)_n$ and $A_2$ is hydroxyl, $C_1$-$C_{18}$alkoxy, $C_5$-$C_6$cycloalkoxy, benzyloxy or benzyloxy substituted by $C_1$-$C_4$alkyl and/or halogen, —$N(R_7)(R_{7a})$ or —$G_1$—$(G_3)_n$, where $G_1$ and n are as defined above, $G_2$ is a radical of the formula

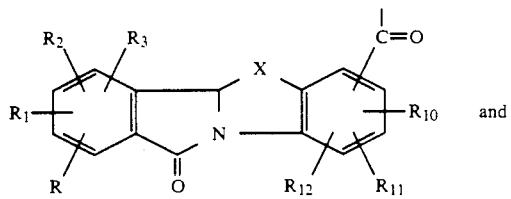

$G_3$ is a radical of the formula

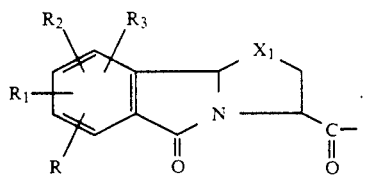

Advantageous compositions contain compounds of the formula I in which R is hydrogen, chlorine, hydroxyl or $C_1$-$C_4$alkyl, $R_1$ is hydrogen, chlorine, $C_1$-$C_4$alkyl or hydroxyl, $R_2$ and $R_3$ are hydrogen, $R_5$ and $R_6$ together form a group of the formula IV, V, VI or VII, $R_9$, $R_{10}$, $R_{11}$ and $R_{12}$ have the same possibilities of meaning as R, $R_1$, $R_2$ and $R_3$ (in this sequence), $R_{13}$ is hydrogen, $C_1$-$C_{18}$alkyl, $C_5$-$C_6$cycloalkyl, benzyl, $C_2$-$C_{19}$alkoxycarbonyl-$C_1$-$C_4$alkyl, carboxy-$C_1$-$C_4$alkyl, $C_2$-$C_{18}$alkanoyl or benzoyl, $R_{14}$, $R_{15}$, $R_{16}$, $R_{17}$, $R_{18}$ and $R_{19}$ are hydrogen and $A_2$ is hydroxyl, $C_1$-$C_{18}$alkoxy, $C_5$-$C_6$cycloalkoxy or benzyloxy.

Compositions which contain compounds of the formula I are preferred in which R and $R_9$ independently of one another are hydrogen, $C_1$-$C_4$alkyl or chlorine and $R_1$, $R_2$, $R_3$, $R_{10}$, $R_{11}$, $R_{12}$, $R_{14}$, $R_{15}$, $R_{16}$, $R_{17}$, $R_{18}$ and $R_{19}$ are hydrogen, and also those in which A, $A_1$ and $A_2$ are different from —$G_1$-$(G)_n$, —$G_1$-$(G_2)_n$ or —$G_1$-$(G_3)_n$.

Particularly preferred compositions contain compounds of the formula I in which R is hydrogen, methyl or chlorine, $R_1$, $R_2$ and $R_3$ are hydrogen, and $R_5$ and $R_6$ together are a group of the formula IV, V, VI or VII in which X is —S—,

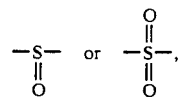

$X_1$ is —S—, $X_2$ is —$CH_2$—, $R_9$ is hydrogen, —$CH_3$, Cl or —COO—($C_1$-$C_{24}$alkyl), $R_{10}$, $R_{11}$ and $R_{12}$ are hydrogen, $R_{13}$ is hydrogen, $C_1$-$C_{18}$alkyl, benzoyl, $C_2$-$C_{19}$alkoxycarbonyl-methyl or $C_2$-$C_{18}$alkanoyl, $R_{14}$ to $R_{19}$ are hydrogen and $A_2$ is $C_1$-$C_{24}$alkoxy.

In contrast to inorganic substances, which are usually stable up to high temperatures, the special feature of organic substances is that they are easily decomposed under the influence of heat, light or radiation, mechanical loading (in particular by shear forces) and chemical reagents (particularly atmospheric oxygen).

The compounds of the formula I, which should expediently be present in the compositions according to the invention to 0.01 to 10, for example to 0.05 to 5, preferably to 0.05 to 3, but in particular to 0.1 to 2% by weight in the organic materials, serve to protect from such influences. One or more of these compounds can be present in the compositions, and the percentage by weight data relate to the total amount of these compounds. The basis of calculation is in this case the total weight of the organic material without the compounds of the formula I.

The materials contained in the compositions according to the invention are those which are sensitive to oxidative, thermal and/or actinic degradation. Living organisms are to be understood as not coming under these organic materials.

The following preferably do not come under the definition "organic material": gelatin- and silver halide-containing photographic emulsions.

Examples of organic materials which may be mentioned which can be stabilised according to the invention with the aid of the compounds of the formula I are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene; as well as polyethylene (which additionally if desired can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene copolymers, linear low-density polyethylene (LLDPE) and its mixtures with low-density polyethylene (LDPE), propylene/but-1-ene copolymers, propylene/isobutylene copolmers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers) and terpolymers of ethylene with propylene and a diene, such as hexadiene, dicyclopentadiene or ethylidenenorbornene; as well as mixtures of such copolymers with each other and with polymers mentioned in 1), for example polypropylene/ethylene-propylene copolymers, LDPE/ethylene-vinylacetate copolymers, LDPE/ethylene-acrylic acid copolymers, LLDPE/ethylene-vinylacetate copolymers and LLDPE/ethylene acrylic acid copolymers.

3a. Hydrocarbon resins (for example $C_5$-$C_9$) and hydrogenated modifications thereof (for example tackifier resins).

4. Polystyrene, poly-(p-methylstyrene), poly-(α-methylstyrene).

5. Copolymers of styrene or α-methylstyrene with dienes or acrylic derivatives, for example, styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength from copolymers of styrene and another polymer, such as, for example, from a polyacrylate, a diene polymer or an ethylene/propylene/diene terpolymer; and block copolymers of styrene, for example, styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene: styrene on copolymers of polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkylacrylates or polyalkylmethacrylates; styrene and acrylonitrile on acrylate/butadiene copolymers, as well as mixtures thereof with the copolymers listed under 5), for example those known as so-called ABS, MBS, ASA and AES polymers.

7. Halogen-containing polymers, such as polychloroprene, chlorinated rubber, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example, acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1).

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain comonomers, ethylene oxide for example; polyacetals modified with thermoplastic polyurethanes, acrylates or MBS.

13. Polyphenylene oxides and sulfides, and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, 6/9, 6/12 and 4/6, polyamide 11, polyamide 12, aromatic polyamides obtained starting from m-xylenediamine and adipic acid; polyamides prepared from hexamethylenediamine and isophthalic and/or terephthalic acid and if desired an elastomer as modifier, for example poly-2,4,4-trimethyl-hexamethylene terephthalamide or poly-m-phenylene-isophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM or ABS; as well as polyamides condensed during processing (RIM-polyamide systems).

16. Polyureas, polyimides, polyamide-imides and polybenzimidazoles.

17. Polyesters which are derived from dicarboxylic acids and dialcohols and/or from hydroxy-carboxylic acids or the corresponding lactones, such as polyethylene terephthalate, polybutylene terephthalate, poly-1,4-dimethylolcyclohexane terephthalate, polyhydroxybenzoate, as well as block polyether-esters derived from polyethers having hydroxyl end groups; in addition polyesters modified with polycarbonates or MBS.

18. Polycarbonates and polyester-carbonates.

19. Polysulfones, polyether-sulfones and polyether-ketones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins, derived from substituted acrylic esters, for example epoxy-acrylates, urethane-acrylates or polyester-acrylates.

24. Alkyd resins, polyester resins or acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Natural polymers, such as cellulose, rubber, gelatin and derivatives thereof which are chemically modified in a polymer-homologous manner, such as cellulose acetates, cellulose propionates and cellulose butyrates, or cellulose ethers, such as methylcellulose; and rosins and their derivatives.

27. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6/6 and copolymers, PA/HDPE, PA/PP, PA/PPO.

28. Naturally occurring and synthetic organic materials which are pure monomeric compounds or mixtures of such compounds, for example mineral oils, animal and vegetable fats, oil and waxes, or oils, waxes and fats based on synthetic esters (e.g. phthalates, adipates, phosphates or trimellitates) and also mixtures of synthetic esters with mineral oils in any weight ratio, which mixtures may be used as spinning preparations, as well as aqueous emulsions thereof.

29. Aqueous emulsions of natural or synthetic rubbers, for example natural latex or latices of carboxylated styrene/butadiene copolymers.

As organic material, the compositions according to the invention preferably contain natural, semisynthetic or synthetic polymers, a lubricant, a metal processing fluid or a hydraulic fluid. Compositions are particularly preferred which contain a synthetic polymer, in particular a thermoplastic or an elastomer. Compositions are to be emphasized in particular which, as an organic material, comprise a polyolefin. Examples of such polymers are to be taken from the above enumeration of suitable materials.

Compositions are also preferred which contain a lubricant, a metal processing fluid or a hydraulic fluid, in particular a lubricant.

Suitable lubricants are based, for example, on mineral or synthetic oils or mixtures thereof. The lubricants are familiar to the person skilled in the art and are described in the relevant specialist literature. for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopaedia of Industrial Chemistry], vol. 13, pages 85-94 (Verlag Chemie, Weinheim, 1977).

The lubricants are in particular oils and fats, for example based on a mineral oil. Oils are preferred.

A further group of lubricants which can be used are vegetable or animal oils, fats, tallows and waxes or mixtures thereof with each other or mixtures with the mineral or synthetic oils mentioned. Vegetable and animal oils, fats, tallows and waxes are, for example, palm kernel oil, palm oil, olive oil, rapeseed oil or rape oil, linseed oil, groundnut oil, soya bean oil, cotton oil, sunflower oil, pumpkin seed oil, coconut oil, maize oil, castor oil, walnut oil and mixtures thereof, fish oils, tallow from slaughtered animals such as bovine tallow, neatsfoot oil and bone oil and their modified, epoxidised and sulfoxidised forms, for example epoxidised soya bean oil.

The mineral oils are based in particular on hydrocarbon compounds.

Examples of synthetic lubricants include lubricants based on aliphatic or aromatic carboxylic esters, the polymeric esters, the polyalkylene oxides, the phosphoric acid esters, the poly-α-olefins or the silicones, on a diester of a dibasic acid with a monohydric alcohol, for example dioctyl sebacate or dinonyl adipate, on a triester of trimethylolpropane with a monobasic acid or with a mixture of such acids, for example trimethylolpropane tripelargonate, trimethylolpropane tricaprylate or mixtures thereof, on a tetraester of pentaerythritol with a monobasic acid or with a mixture of such as acids, such as, for example, pentaerythritol tetracaprylate, or on a complex ester of monobasic and dibasic acids with polyhydric alcohols, for example a complex ester of trimethylolpropane with caprylic and sebacic acid or on a mixture thereof. Particularly suitable in addition to mineral oils are, for example, poly-α-olefins, lubricants based on esters, phosphates, glycols, polyglycols and polyalkylene glycols, and mixtures thereof with water.

Metal processing fluids and hydraulic fluids can be prepared based on the same substances as described above for the lubricants. Frequently, these are also emulsions of such substances in water or other fluids.

Incorporation into the organic materials can be carried out, for example, by mixing in the compounds of the formula I and, if desired, other additives by the methods customary in industry. If they are polymers, in particular synthetic polymers, incorporation can be carried out before or during moulding, or by applying the dissolved or dispersed compounds to the polymers, if appropriate with subsequent evaporation of the solvent. In the case of elastomers, these can also be stabilised as latices. A further possibility for incorporation of the compounds of the formula I in polymers comprises their addition before or during polymerisation of the corresponding monomers or before crosslinking. In the case of addition before or during polymerisation, the compounds of the formula I can also act as regulators for the chain length of the polymers (chain terminators).

The compounds of the formula I or mixtures thereof can also be added to the plastics to be stabilised in the form of a masterbatch which contains these compounds, for example, in a concentration of 2.5 to 25% by weight.

The incorporation of the compounds of the formula I can expediently be carried out by the following methods:

as an emulsion or dispersion (for example to give latices or emulsion polymers)

as a dry mixture during mixing of additive components or polymer mixtures by direct addition to the processing apparatus (for example extruders, internal mixers etc.)

as a solution or melt.

Polymer compositions according to the invention can be used in various forms or processed to give various products, for example as (to give) foils, fibres, tapes, moulded materials, profiles or as binders for paints, adhesives or cement.

Lubricant compositions according to the invention are used, for example, in internal combustion motors, for example in motor vehicles.

In addition to the compounds or mixtures according to the invention, the compositions according to the invention can contain still other customary additives, in particular if they contain organic, preferably synthetic polymers. Examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol),2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl) carbamate.

1.7. Esters of $\beta$-(3,5-di-tert-butyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.8. Esters of $\beta$-(5-tert-butyl-4-hydroxy-3-methylphenyl)propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'bis(hydroxyethyl)oxalic acid diamide.

1.9. Esters of $\beta$-(3,5-dicyclohexyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.10. Amides of $\beta$-(3,5-di-tert-butyl-4-hydroxyphenyl)propionic acid for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis($\alpha,\alpha$-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides, and o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic-dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, fluorescent whitening agents, flameproofing agents, antistatic agents and blowing agents.

If the compositions according to the invention are those based on lubricants and hydraulic fluids or metal processing fluids, they can also contain other additives which are added to improve certain use properties, for example other antioxidants, metal deactivators, rust inhibitors, viscosity index improvers, pour point reducers, dispersants/surfactants and abrasion resistance additives.

Examples of antioxidants are to be taken from the listing reproduced further above under the title "1. Antioxidants", in particular items 1.1 to 1.10. Examples of other additional additives are the following:

Examples of amine antioxidants: N,N'-di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, such as p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)-amine, 2,6-di-tert-butyl-4-dimethylamino-methylphenol, 2,4'-diamino-diphenylmethane, 4,4'-diamino-diphenylmethane, N,N,N',N'-tetramethyl-4,4'-diamino-diphenylmethane, 1,2-di-[(2-methyl-phenyl)-amino]-ethane, 1,2-di-(phenylamino)-propane, (o-tolyl)-biguanide, di-[4-(1',3'-dimethyl-butyl)-phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of other antioxidants: aliphatic or aromatic phosphites, esters of thiodipropionic acid or thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidenepropylenediamine, salicylaminoguanidine and salts thereof.

Examples of rust inhibitors are:

a) Organic acids, their esters, metal salts and anhydrides, for example: N-oleoylsarcosine, sorbitan monooleate, lead naphthenate, alkenylsuccinic anhydride, for example dodecylsuccinic anhydride, alkenylsuccinic acid partial esters and partial amines, 4-nonylphenoxyacetic acid.

b) Nitrogen-containing compounds, for example:
  i. Primary, secondary or tertiary aliphatic or cycloaliphatic amines and amine salts of organic and inorganic acids, for examples oil-soluble alkylammonium carboxylates.
  ii. Heterocyclic compounds, for example: substituted imidazolines and oxazolines.

c) Phosphorus-containing compounds, for example: amine salts of phosphoric acid partial esters or phosphonic acid partial esters, zinc dialkyldithiophosphates.

d) Sulfur-containing compounds, for example: barium dinonylnaphthalenesulfonates, calcium petroleumsulfonates.

Examples of viscosity index improvers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour point reducers are: polymethacrylate, alkylated naphthalene derivatives.

Examples of dispersants/surfactants are: polybutenylsuccinamides or -imides, polybutenylphosphoric acid derivatives, basic magnesium, calcium, and barium sulfonates and phenolates.

Examples of abrasion resistance additives are: sulfur- and/or phosphorus- and/or halogen-containing compounds, such as sulfurised vegetable oils, zinc dialkyldithiophosphates, tritolyl phosphate, chlorinated paraffins, alkyl and aryl di- and tri-sulfides, triphenyl phosphorothionates, diethanolaminomethyltolyltriazole, di(2-ethylhexyl)aminomethyltolyltriazole.

It is particularly advantageous to employ the compounds of the formula I in combination with organic phosphites or phosphonites, in particular for the stabilisation of thermoplastic polymers. The invention therefore also relates to compositions which contain at least one compound of the formula I and at least one organic phosphite and/or phosphonite. Examples of such phosph(on)ites are those of the formulae

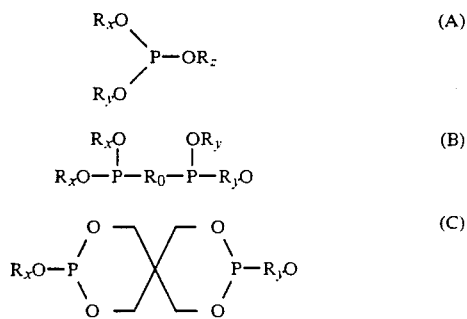

in which $R_x$, $R_y$ and $R_z$ independently of one another are $C_6$-$C_{20}$alkyl, $C_5$-$C_8$cycloalkyl, phenyl or phenyl substituted by one to three $C_1$-$C_{12}$alkyl and $R_0$ is phenylene, naphthylene or diphenylene which is unsubstituted or substituted by $C_1$-$C_{12}$alkyl or is a radical —O—$R_v$—O—, in which $R_v$ is phenylene, naphthylene or diphenylene which is unsubstituted or substituted by $C_1$-$C_{12}$alkyl or $R_0$ is a radical -phen-$R_w$-phen- in which phen is phenylene and $R_w$ is —O—, —S—, —SO$_2$—, —CH$_2$— or —C(CH$_3$)$_2$—.

Among the compounds of the formula A, those are preferred in which $R_x$, $R_y$ and $R_z$ are $C_6$-$C_{20}$alkyl, phenyl or phenyl substituted by one to three, in particular one to two, $C_1$-$C_{12}$alkyl groups.

Among the compounds of the formula B, those are preferred in which $R_x$ and $R_y$ are phenyl or phenyl substituted by one to two $C_1$-$C_{12}$alkyl groups and $R_0$ is a diphenylene radical.

Among the compounds of the formula C, those are preferred in which $R_x$ and $R_y$ are phenyl or phenyl which is substituted by one to three $C_1$-$C_{12}$alkyl groups.

Phosphites and phosphonites which contain at least one P—O—Ar group are preferably used, Ar being a mono- or dialkylphenyl radical. Examples of these are: triphenyl phosphite, decyl diphenyl phosphite, phenyl didecyl phosphite, tris(nonylphenyl) phosphite, trilauryl phosphite, trioctadecyl phosphite, distearyl pentaerythritol diphosphite, tris(2,4-di-tert-butylphenyl) phosphite, diisodecylpentaerythritol diphosphite, bis(2,4-di-tert-butylphenyl)pentaerythritol diphosphite, tristearylsorbitol triphosphite, tetrakis(2,4-di-tert-butylphenyl)-4,4'-biphenylene diphosphonite, bis(2,6-di-tert-butyl-4-methylphenyl)pentaerythritol diphosphite.

The amount of phosph(on)ite added depends on the amount of compound of the formula I added. In general, 0.01 to 1% by weight, in particular 0.05 to 0.5% by weight, is used, relative to the polymer.

The invention further relates to novel isoindolinone compounds which have the formula X

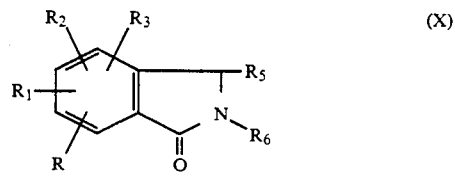

in which R is hydrogen, $C_1$-$C_{18}$alkyl, $C_1$-$C_{18}$alkoxy, halogen, nitro, phenyl-$C_1$-$C_4$alkoxy, $C_2$-$C_{18}$alkanoyl, benzoyl, ($C_1$-$C_6$alkyl)benzoyl, $C_2$-$C_{18}$alkenoyl, —N($R_7$)($R_{7a}$), —OH or —CO—A, $R_1$ has the same possibilities of meaning as R, $R_2$ is hydrogen or $C_1$-$C_4$alkyl and $R_3$ is hydrogen or halogen, A is hydroxyl, $C_1$-$C_{18}$alkoxy, $C_5$-$C_{12}$cycloalkoxy, benzyloxy or benzyloxy substituted by $C_1$-$C_4$alkyl and/or halogen, —N($R_7$)($R_{7a}$), —NH—NH—$R_8$ or —$G_1$—(G)$_n$, n is a number from 1 to 3 and G is a radical of the formula

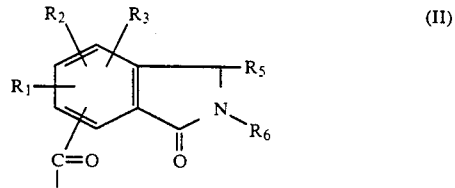

$G_1$ in the case where n=1 is —O—$R_{20}$—O—, —NH—$R_{21}$—NH— or —NH—NH—, in the case where n=2 is a group of the formula

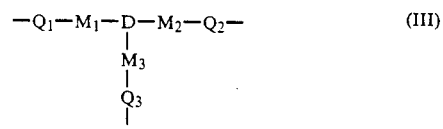

and in the case where n=3 is (—O—CH$_2$)$_4$C or

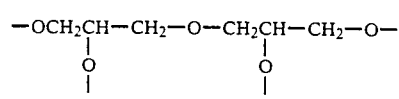

where D is N, CH or C($C_1$-$C_4$alkyl), $Q_1$, $Q_2$ and $Q_3$ independently of one another are O or NH and $M_1$, $M_2$ and $M_3$ independently of one another are $C_1$-$C_6$alkylene or $C_2$-$C_{12}$alkylene which is interrupted by —O—, or in the case where D=CH or C($C_1$-$C_4$alkyl) —M$_3$—Q$_3$ is also —O— or in the case where D=N —M$_3$—Q$_3$ is also a direct bond, $R_5$ and $R_6$ together form a group of the formula IV, V or VII

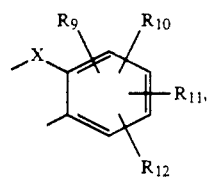
(IV)

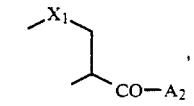
(V)

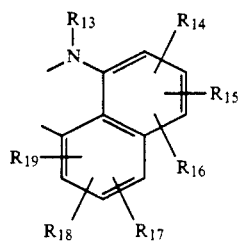
(VII)

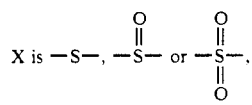
X is —S—, $-\overset{O}{\underset{}{S}}-$ or $-\overset{O}{\underset{O}{S}}-$,

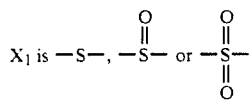
$X_1$ is —S—, $-\overset{O}{\underset{}{S}}-$ or $-\overset{O}{\underset{O}{S}}-$ where if X is S or S=O and one of the substituents $R_9$-$R_{12}$ is H, alkoxy or halogen, the remaining 3 of these substituents cannot simultaneously be H, $R_7$ and $R_{7a}$ independently of one another are hydrogen, $C_1$-$C_{18}$alkyl, phenyl-$C_1$-$C_4$alkyl, $C_2$-$C_{18}$alkanoyl, $C_2$-$C_{18}$alkenoyl, $C_2$-$C_4$hydroxyalkyl, benzoyl or ($C_1$-$C_6$alkyl)benzoyl or, together with the N atom to which they are bonded, are piperidyl, morpholinyl, piperazinyl or 4-methylpiperazinyl, $R_8$ is hydrogen, $C_2$-$C_{18}$alkanoyl, benzoyl or ($C_1$-$C_6$alkyl)benzoyl, $R_9$, $R_{10}$, $R_{11}$ and $R_{12}$ have the same possibilities of meaning as R, $R_1$, $R_2$ and $R_3$ (in this sequence), where —CO—A is to be replaced by —CO—$A_1$, $R_{13}$ is hydrogen, $C_1$-$C_{18}$alkyl, $C_2$-$C_{18}$alkenyl, $C_5$-$C_{12}$cycloalkyl, phenyl-$C_1$-$C_4$alkyl, $C_2$-$C_{18}$alkanoyl, $C_2$-$C_{18}$alkenoyl, benzoyl, ($C_1$-$C_6$alkyl)benzoyl, benzyl, $C_2$-$C_{19}$alkoxycarbonyl-$C_1$-$C_4$alkyl, carboxy-$C_1$-$C_4$alkyl, cyano-$C_1$-$C_4$alkyl, hydroxy-$C_2$-$C_4$alkyl or

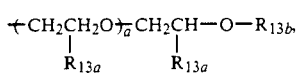

$R_{13a}$ is hydrogen or methyl and $R_{13b}$ is hydrogen, $C_1$-$C_{18}$alkyl, phenyl-$C_1$-$C_4$alkyl, $C_2$-$C_{18}$alkanoyl, benzoyl, $C_2$-$C_{18}$alkenoyl or ($C_1$-$C_6$alkyl)benzoyl and a is a number from 0 to 6, $R_{14}$, $R_{15}$, $R_{16}$, $R_{17}$, $R_{18}$ and $R_{19}$ independently of one another are hydrogen, $C_1$-$C_4$alkyl, halogen, hydroxyl, $C_1$-$C_{18}$alkoxy or —N($R_{7b}$)($R_{7c}$), in which $R_{7b}$ and $R_{7c}$ independently of one another are hydrogen or $C_1$-$C_{18}$alkyl, $R_{20}$ is $C_1$-$C_{12}$alkylene, $C_2$-$C_8$alkenylene, $C_3$-$C_6$alkynylene or $C_2$-$C_{24}$alkylene interrupted by O, S and/or —N($R_{22}$)—, $R_{21}$ is $C_1$-$C_{12}$alkylene and $R_{22}$ is hydrogen, $C_1$-$C_{18}$alkyl, phenyl, ($C_1$-$C_6$-alkyl)phenyl or phenyl-$C_1$-$C_4$alkyl, $A_1$ is hydroxyl, $C_1$-$C_{24}$alkoxy, $C_5$-$C_{12}$cycloalkoxy, benzyloxy or benzyloxy substituted by $C_1$-$C_4$alkyl and-/or halogen, —N($R_7$)($R_{7a}$), —NH—NH—$R_8$ or —$G_1$—($G_2$)$_n$, and $A_2$ is hydroxyl, $C_1$-$C_{24}$alkoxy, $C_5$-$C_{12}$cycloalkoxy, benzyloxy or benzyloxy substituted by $C_1$-$C_4$alkyl and/or halogen, —N($R_7$)($R_{7a}$), —NH—NH—$R_8$ or —$G_1$—($G_3$)$_n$, where $G_1$ and n are as defined above, $G_2$ is a radical of the formula

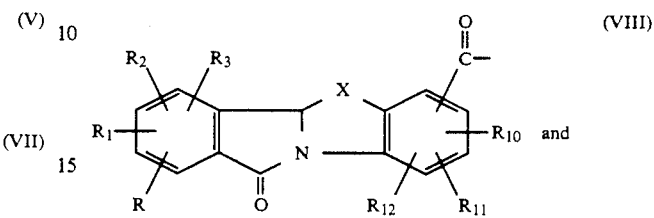
(VIII)

$G_3$ is a radical of the formula

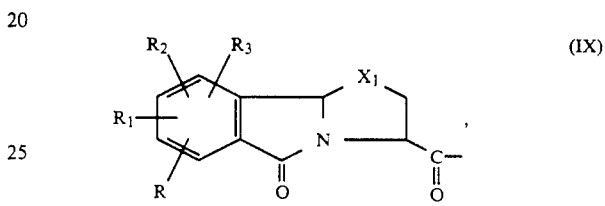
(IX)

with the provisos, (1) that only one substituent —CO—A, CO—$A_1$ or —CO—$A_2$ is present in the molecule, in which A, $A_1$ or $A_2$ is a radical —$G_1$—(G)$_n$, —$G_1$—($G_2$)$_n$ or —$G_1$—($G_3$)$_n$ and (2) that in the case where X=S a maximum of one of these substituents R and $R_1$ is $C_1$-$C_{18}$alkoxy.

Advantageous compounds of the formula X are those in which R is hydrogen, hydroxyl, $C_1$-$C_4$alkyl, chlorine, nitro, $C_1$-$C_4$alkoxy, benzoyl, —N($R_7$)($R_{7a}$) or —CO—A, $R_1$ has the same possibilities of meaning as R, $R_2$ is hydrogen, chlorine or $C_1$-$C_4$alkyl and $R_3$ is hydrogen or chlorine, A is hydroxyl, $C_1$-$C_{18}$alkoxy, $C_5$-$C_6$cycloalkoxy, benzyloxy or benzyloxy substituted by $C_1$-$C_4$alkyl and/or chlorine, —N($R_7$)($R_{7a}$) or —$G_1$—(G)$_n$, n is a number from 1 to 3 and G is a radical of the formula

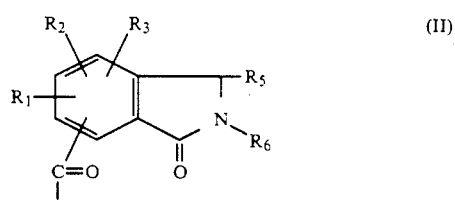
(II)

$G_1$ in the case where n=1 is —O—$R_{20}$—O— or —NH—$R_{21}$—NH—, in the case where n=2 is a group of the formula

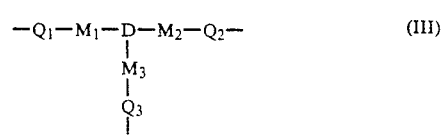
(III)

and in the case where n=3 is (—OCH$_2$)$_4$C, where D is equal to N, CH or C($C_1$-$C_4$alkyl), $Q_1$, $Q_2$ and $Q_3$ independently of one another are O or NH and $M_1$, $M_2$ and $M_3$ independently of one another are $C_1$-$C_6$alkylene or $C_2$-$C_{12}$alkylene interrupted by —O—, or in the case where D=CH or C($C_1$-$C_4$alkyl) —$M_3$—$Q_3$ is also —O— or in the case where D=N —$M_3$—$Q_3$ is also a direct bond, $R_5$ and $R_6$ together form a group of the formula IV, V or VII, $R_7$ and $R_{7a}$ independently of one another are hydrogen, $C_1$-$C_6$alkyl, benzyl, $C_2$-$C_4$hydroxyalkyl or, together with the N atom to which they are bonded, are piperidyl, morpholinyl, piperazinyl or 4-methylpiperazinyl, $R_9$, $R_{10}$, $R_{11}$ and $R_{12}$ have the same possibilities of meaning as R, $R_1$, $R_2$ and $R_3$ (in this sequence), where —CO—A is to be replaced by —CO—$A_1$, $R_{13}$ is hydrogen, $C_1$-$C_{18}$alkyl, $C_2$-$C_{18}$alkenyl, $C_5$-$C_6$cycloalkyl, phenyl-$C_1$-$C_4$alkyl, $C_2$-$C_{18}$alkanoyl, $C_2$-$C_{18}$alkenoyl, benzoyl, ($C_1$-$C_6$alkyl)benzoyl, cyano-$C_1$-$C_4$alkyl, $C_2$-$C_{19}$alkoxycarbonyl-$C_1$-$C_4$alkyl, carboxy-$C_1$-$C_4$alkyl or hydroxy-$C_2$-$C_4$alkyl, $R_{14}$, $R_{15}$, $R_{16}$, $R_{17}$, $R_{18}$ and $R_{19}$ independently of one another are hydrogen, $C_1$-$C_4$alkyl, chlorine, hydroxyl, $C_1$-$C_4$alkoxy or —N($R_{7b}$)($R_{7c}$), in which $R_{7b}$ and $R_{7c}$ independently of one another are hydrogen or $C_1$-$C_6$alkyl, $R_{20}$ is $C_1$-$C_{12}$alkylene, $C_2$-$C_8$alkenylene, $C_3$-$C_6$alkynylene or $C_2$-$C_{24}$alkylene interrupted by O, S and/or —N($R_{22}$), $R_{21}$ is $C_1$-$C_{12}$alkylene and $R_{22}$ is hydrogen or $C_1$-$C_4$alkyl, $A_1$ is hydroxyl, $C_1$-$C_{18}$alkoxy, $C_5$-$C_6$cycloalkoxy, benzyloxy or benzyloxy substituted by $C_1$-$C_4$alkyl and/or halogen, —N($R_7$)($R_{7a}$) or —G$_1$—(G$_2$)$_n$ and $A_2$ is hydroxyl, $C_1$-$C_{18}$alkoxy, $C_5$-$C_6$cycloalkoxy, benzyloxy or benzyloxy substituted by $C_1$-$C_4$alkyl and/or halogen, —N($R_7$)($R_{7a}$) or —G$_1$—(G$_3$)$_n$, where $G_1$ and n are as defined above, $G_2$ is a radical of the formula

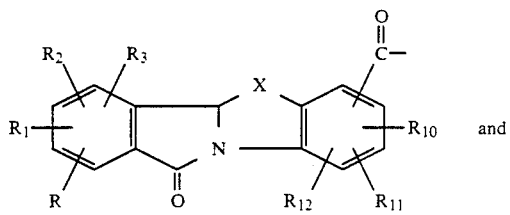

$G_3$ is a radical of the formula

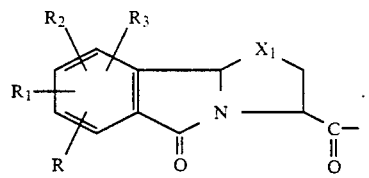

Preferred compounds of the formula X are those in which R is hydrogen, chlorine, hydroxyl or $C_1$-$C_4$alkyl, $R_1$ is hydrogen, chlorine, $C_1$-$C_4$alkyl or hydroxyl, $R_2$ and $R_3$ are hydrogen, $R_5$ and $R_6$ together form a group of the formula IV, V or VII, $R_9$, $R_{10}$, $R_{11}$ and $R_{12}$ have the same possibilities of meaning as R, $R_1$, $R_2$ and $R_3$ (in this sequence), $R_{13}$ is hydrogen, $C_1$-$C_{18}$alkyl, $C_5$-$C_6$cycloalkyl, benzyl, $C_2$-$C_{18}$alkanoyl or benzoyl, $R_{14}$, $R_{15}$, $R_{16}$, $R_{17}$, $R_{18}$ and $R_{19}$ are hydrogen, and $A_2$ is hydroxyl, $C_1$-$C_{18}$alkoxy, $C_5$-$C_6$cycloalkoxy or benzyloxy, in particular those in which R is hydrogen, methyl or chlorine, $R_1$, $R_2$ and $R_3$ are hydrogen, and $R_5$ and $R_6$ together are a group of the formula IV, V or VII, in which X is —S—,

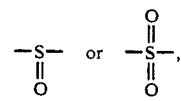

$X_1$ is —S—, $R_9$ is hydrogen, —$CH_3$, Cl or —COO—($C_1$-$C_{24}$alkyl), $R_{10}$, $R_{11}$ and $R_{12}$ are hydrogen, $R_{13}$ is hydrogen, $C_1$-$C_{18}$alkyl, benzoyl, $C_2$-$C_{19}$alkoxycarbonylmethyl or $C_2$-$C_{18}$alkanoyl, $R_{14}$ to $R_{19}$ are hydrogen and $A_2$ is $C_1$-$C_{24}$alkoxy.

Particularly preferred compounds of the formula X are those in which R and $R_9$ independently of one another are hydrogen, $C_1$-$C_4$alkyl or chlorine and $R_1$, $R_2$, $R_3$, $R_4$, $R_{10}$, $R_{11}$, $R_{12}$, $R_{14}$, $R_{15}$, $R_{16}$, $R_{17}$, $R_{18}$ and $R_{19}$ are hydrogen.

The invention further relates to the use of compounds according to the formulae I and X for stabilising organic material against oxidative, thermal and/or actinic degradation.

The use of compounds according to the formulae I and X as stabilisers in lubricants, metal processing fluids and hydraulic fluids and in synthetic, natural or semisynthetic polymers is preferred.

The invention accordingly also comprises a process for stabilising organic material, in particular lubricants, metal processing fluids and hydraulic fluids and natural, synthetic or semisynthetic polymers, which comprises adding compounds of the formula I or X to this material as stabilisers or applying them to this.

The compounds according to the invention and the isoindolinone compounds employed in the compounds according to the invention are prepared, for example, by the processes described in C. H. Gaozza et al., J. Heterocycl. Chem. 9, 883 (1972) and U.S. Pat. No. 3,591,599 and can be summarised by the following reaction scheme:

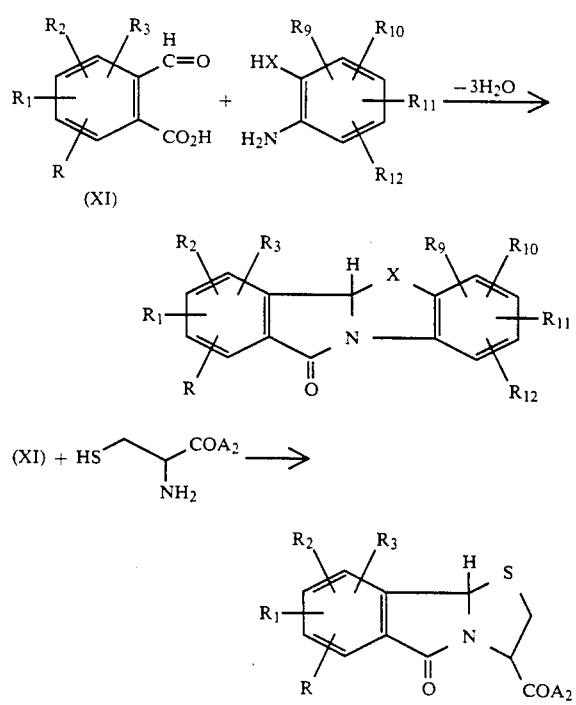

-continued

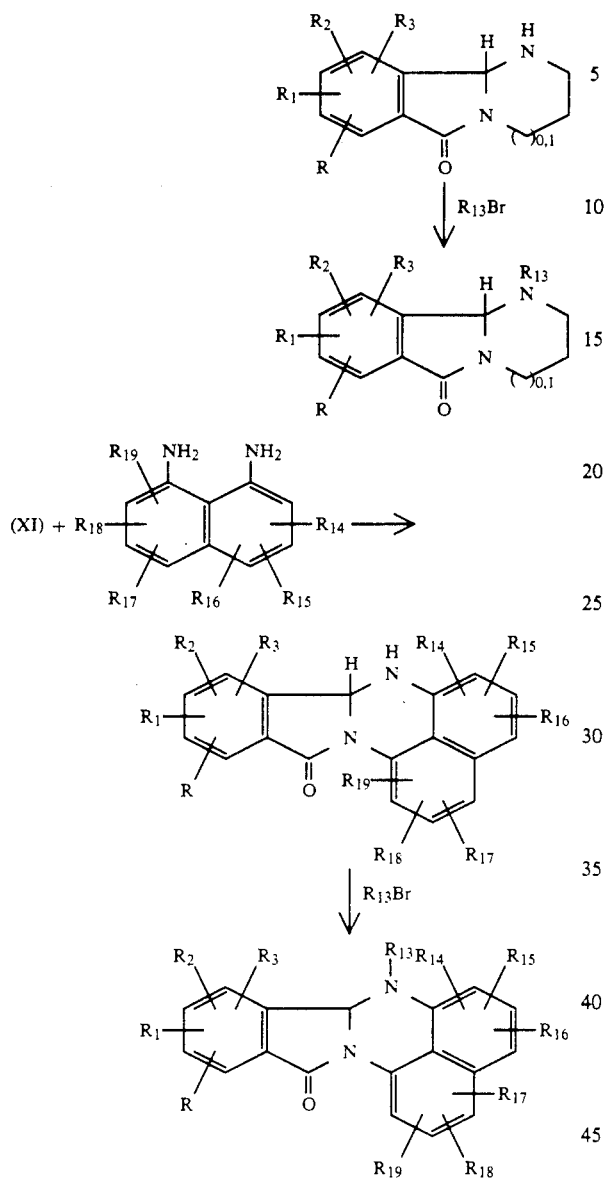

The reactions are expediently carried out with the addition of customary solvents which are inert under the reaction conditions, preferably ethanol. The sulfur-containing products can be oxidised to the corresponding sulfoxide and sulfone compounds using oxidising agents. m-Chloroperbenzoic acid, for example, is preferred as an oxidising agent.

Of course, after ring construction has taken place, possible substituents can be converted into one another or introduced by customary processes known in organic chemistry.

To prepare compounds of the formula I in which A, $A_1$ or $A_2$ are —$G_1$—$(G)_n$, —$G_1$—$(G_2)_n$ or —$G_1$—$(G_3)_n$ in the radicals —COA, —$COA_1$ or —$COA_2$, the corresponding acids (A, $A_1$, $A_2$=OH), for example, are used as starting materials and the reaction (oligomerisation) is carried out from the esters or amides formed therefrom.

If oligomerisation takes place via esters, this is carried out, for example, by conversion of the free acid (A, $A_1$, $A_2$=OH) into the corresponding acid chloride (for example with $PCl_5$, $SOCl_2$) and reaction with the di-, tri- or tetrahydric alcohol corresponding to the radical $G_1$, preferably with base catalysis. The acid can also be reacted with the corresponding higher valency alcohol directly in the presence of heat, or else gently by treatment with dicyclohexylcarbodiimide (DCC) in the presence of the higher valency alcohol (Tetrahedron Letters 1978, 4475-8), or by further gentle processes described, for example, in Tetrahedron 36, 2409 (1980). A further possibility to obtain the compounds oligomerised via ester groups comprises esterification with a diol, triol or tetraol starting from the lower monoesters. Catalysts suitable for this are, for example, strong acids such as $H_2SO_4$, HCl, p-toluenesulfonic acid, methanesulfonic acid, acid ion exchangers or alternatively bases, for example $LiNH_2$, $CH_3ONa$ or else dialkyltin oxides or titanium tetraalkoxylates. The lower alcohol is removed from the reaction mixture by distillation in this case. The amount of catalyst is as a rule 0.1-5 mol %, relative to the monoester.

If oligomerisation takes place via amides, the acid chlorides are formed as described above and are then reacted with the di- or triamine corresponding to a radical $G_1$. In the case of sensitive compounds, for example, the method using DCC is also suitable in addition to the other processes described in Tetrahedron 36, 2409 (1980). In addition, lower esters (A, $A_1$, $A_2$=methyl, ethyl, isopropyl, propyl, etc.) can be reacted directly with the amines mentioned to give the corresponding amines in the presence of heat.

The reactions can be carried out with or without addition of customary inert solvents. Some of the preparation processes described are illustrated in detail in the following examples.

The starting compounds required for the preparation processes described above are known or can be prepared by customary methods in a manner known per se.

The following examples illustrate the invention further. If not stated otherwise, parts and percentage data therein and in the remaining description are parts by weight and percentages by weight.

EXAMPLE 1

Compound 1, Table 1

12.5 g of 2-aminothiopenyl and 15.0 g of phthaladehydic acid are boiled under nitrogen for 12 hours in 100 ml of ethanol. The reaction mixture is then cooled, and the precipitated solid is filtered off with suction and recrystallised from ethanol/methylene chloride (1:1). 18.2 g of colourless crystals of melting range 173°-174° C. are thus obtained, which correspond to the structure of compound 1.

EXAMPLE 2

Compound 2, Table 1

6.25 g of 3-amino-4-mercaptobenzoic acid and 5.54 g of phthalaldehydic acid are boiled under nitrogen for 17 hours in 40 ml of ethanol and 10 ml of water. The reaction mixture is then cooled and the precipitated solid is filtered off with suction and dried. 6.9 g of white crystals of melting point 256°-260° C. are thus obtained. 4.8 g of this compound are stirred at room temperature for 20 hours in 50 ml of methylene chloride with 4.58 g of stearyl alcohol, 3.5 g of dicyclohexylcarbodiimide and 0.1 g of 4-dimethylaminopyridine. The reaction mixture is then filtered, the filtrate is evaporated on a rotary evaporator and the residue is recrystallised from acetonitrile. 6.7 g of colourless crystals of melting range 93°–95° C. are thus obtained, which correspond to the structure of compound 2.

EXAMPLE 3

Compound 3, Table 1

1.86 g of L-cysteine ethyl ester hydrochloride and 1.50 g of phthalaldehydic acid are boiled under nitrogen for 4 hours in 20 ml of ethanol. The reaction mixture is then evaporated on a rotary evaporator, the residue is treated with 2.70 g of stearyl alcohol and 0.05 g of p-toluenesulfonic acid and the mixture is then stirred at 200° C. for 90 min in a weak vacuum (20 kPa). After cooling, column chromatography on silica gel (methylene chloride/hexane=19:1) and recrystallization from acetonitrile, 3 g of the compound 3 are obtained having a melting point of 51°–3° C.

EXAMPLE 4

Compound 4, Table 1

12.0 g of the compound 1 in 120 ml of methylene chloride are cooled to −30° C. and treated at this temperature with 10.2 g of m-chloroperbenzoic acid (85%). The temperature of the reaction mixture is then increased to +20° C. in the course of 3 hours. The mixture is then washed with 1N KOH and then with water and evaporated on a rotary evaporator. 8.35 g of the compound 4 having a melting point range of 178°–82° C. are obtained from the residue by chromatography on silica gel (methylene chloride/ethyl acetate=19:1).

EXAMPLE 5

Compound 5, Table 1

9.59 g of the compound 1 are oxidised at 20° C. for 20 hours using 24.0 g of m-chloroperbenzoic acid (85%) as described in Example 4. 9.4 g of the compound 5, which melts between 214° and 216° C., are obtained by crystallisation from toluene.

EXAMPLE 6

Compound 6, Table 1

7.41 g of diaminopropane and 15.01 g of phthalaldehydic acid are dissolved in 100 ml of ethanol and the mixture is boiled under nitrogen for 3 hours. The solvent is then removed by distillation and the residue is recrystallised from toluene/hexane (1:1). 16.41 g of the compound 6, which melts between 128° and 130° C., are thus obtained.

EXAMPLE 7

Compound 7, Table 1

9.4 g of the compound 6, 15.56 g of cetyl bromide and 0.1 g of potassium iodide are boiled under nitrogen for 15 hours in 50 ml of dimethylformamide. The reaction mixture is then cooled, diluted with 50 ml of methylene chloride and washed 3× with 500 ml of water. 5.7 g of the compound 7 of melting range 50°–51° C. are obtained from the residue, after evaporating off the methylene chloride, by chromatography on silica gel (methylene chloride/ethyl acetate 1:1) and subsequent crystallisation from hexane.

EXAMPLE 8

Compound 8, Table 1

6.63 g of the compound 6 are dissolved in 20 ml of pyridine and the solution is treated with 4.92 g of benzoyl chloride and 0.5 g of 4-dimethylaminopyridine. The reaction mixture is stirred at room temperature for 3 hours, then it is diluted with 100 ml of methylene chloride, and washed with water, dilute hydrochloric acid and again with water. The residue is crystallised from methanol after evaporating off the solvent. 7.4 g of the compound 8 of melting point 143°–5° C. are thus obtained.

EXAMPLES 9 AND 10

Compounds 9 and 10, Table 1

15.82 g of 1,8-diaminonaphthalene and 15.02 g of phthalaldehydic acid are dissolved in 150 ml of ethanol and the solution is boiled under nitrogen for 1 hour. The reaction mixture is then cooled and the precipitated solid is filtered off with suction, washed with ethanol and dried. 24.7 g of the intermediate of melting range 230°–240° C. are thus obtained (compound 9).

10.0 g of the above intermediate are dissolved in 30 ml of dimethylformamide and the solution is then treated with 12.33 g of cetyl bromide and 1.0 g of potassium iodide and the mixture is boiled under nitrogen for 24 hours. The reaction mixture is then diluted with 100 ml of methylene chloride and washed with water. 12.8 g of the compound 10, which melts between 54° and 56° C., are obtained from the residue after evaporating the solvent, by chromatography on silica gel (methylene chloride) and crystallisation from ethanol.

EXAMPLE 11

Compound 11, Table 1

28.2 g of the compound 6, 45 ml of methyl bromoacetate, 1 g of sodium iodide and 20.8 g of potassium carbonate are slowly heated to reflux and boiled for 15 min. The reaction mixture is diluted with 100 ml of toluene and filtered. After evaporing the filtrate in vacuo (150 mbar), the residue is chromatographed on silica gel (ethyl acetate/isopropanol 3:1) and recrystallised from toluene/hexane (1:1). 21.3 g of the compound 11 are obtained. Melting point 70°–73° C.

EXAMPLE 12

Compound 12, Table 1

7.8 g of the compound 11, 5.65 g of n-dodecanol and 0.13 g of dibutyltin oxide are heated to 150° C. for 4 h in a weak vacuum (0.15 bar). 8.7 g of the compound 12 are obtained after cooling and chromatography on silica gel (dichloromethane/ethyl acetate 4:1) and recrystallisation from acetonitrile. Melting point 44°–45° C.

TABLE 1
| No. | Compound | m.p. °C. | C | H | N | S |
|---|---|---|---|---|---|---|
| | | | \[calculated/found\] % | | | |
| 1 | 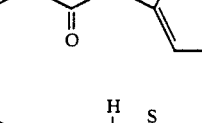 | 173–4 | 70.27<br>70.31 | 3.79<br>3.82 | 5.85<br>5.90 | 13.40<br>13.42 |
| 2 | 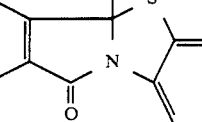 | 93–5 | 73.98<br>73.49 | 8.47<br>8.53 | 2.61<br>2.53 | 5.98<br>6.09 |
| 3 | 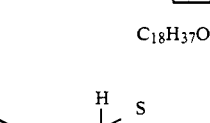 | 51–5 | 71.41<br>72.12 | 9.30<br>9.19 | 2.87<br>2.79 | 6.57<br>6.48 |
| 4 | 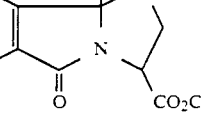 | 178–82 | 65.87<br>65.85 | 3.55<br>3.68 | 5.49<br>5.21 | 12.56<br>12.84 |
| 5 | 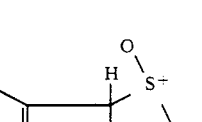 | 214–16 | 61.98<br>62.01 | 3.34<br>3.32 | 5.16<br>4.91 | 11.82<br>11.80 |
| 6 | 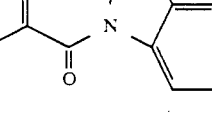 | 128–130 | 70.19<br>70.18 | 6.43<br>6.55 | 14.88<br>15.02 | —<br>— |
| 7 | 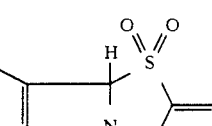 | 50–1 | 78.59<br>78.51 | 10.75<br>10.73 | 6.79<br>6.72 | —<br>— |
| 8 | 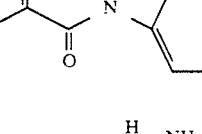 | 143–5 | 73.96<br>73.74 | 5.52<br>5.52 | 9.59<br>9.70 | —<br>— |

TABLE 1-continued

| No. | Compound | m.p. °C | C [calc/found] % | H | N | S |
|---|---|---|---|---|---|---|
| 9 | (structure: isoindolinone fused with naphthalene, NH) | 230–240 | | | | |
| 10 | (structure: N-C$_{16}$H$_{33}$ substituted isoindolinone-naphthalene) | 54–6 | 82.21 / 82.16 | 8.93 / 9.01 | 5.64 / 5.63 | — / — |
| 11 | (structure: isoindolinone with N-CH$_2$CO$_2$CH$_3$, piperidine ring) | 70–73 | 64.60 / 64.65 | 6.20 / 6.20 | 10.76 / 10.92 | — / — |
| 12 | (structure: isoindolinone with N-CH$_2$CO$_2$C$_{12}$H$_{25}$, piperidine ring) | 44–45 | 72.60 / 72.42 | 9.02 / 9.29 | 6.77 / 6.63 | — / — |

EXAMPLE 13

Test for Stabilisation of an Industrial Oil Against Oxidative Degradation

TFOUT: Thin Film Oxygen Uptake Test

This test is a modified form of the rotary bomb test for mineral oils (ASTM D 272). A detailed description can be found in C. S. Ku, S. M. Hsu, Lubrication Engineering 40 (1984) 75–83. The test oil in this case is a commercial 15W40 motor oil, with about half the usual content of zinc dithiophosphates (0.75% ZnDTP, 550 ppm P, 1160 ppm Zn). The additive to be tested (compound of the formula I) is tested for its stabilising effect in the oil in the presence of water (2%), an oxidised/nitrated petroleum fraction (4%) and a mixture of liquid metal naphthenates (4%) at an oxygen pressure of 6.1 bar and 160° C. The water and the two liquid catalysts for the test are obtained from the National Bureau of Standards (NBS), with certification for the analysis, under the designation Standard Reference Material 1817. The test is concluded when a clear kink in the pressure/time graph indicates the oxidation setting in at the end of the induction period (min).

A long induction period denotes a good stabilising effect of the additive. The results are summarised in Table 2.

TABLE 2

| Compound from Example | Amount added (% by weight) | Induction period (min.) |
|---|---|---|
| 9 | 0.5 | 153 |
| Reference | without additive | 83 |

EXAMPLE 14

Test for Stabilisation of the Melt Index of Polypropylene on Multiple Extrusion 1.3 kg of polypropylene powder (melt index 3.2 g/10 min, measured at 230° C. using 2.16 kg) are mixed with 0.05% of calcium stearate and 0.05% of Irganox 1010 and 0.05% of processing stabiliser. This mixture is extruded in an extruder having a cylinder diameter of 20 mm and a length of 20 d=400 mm at 100 rpm, the 3 heating zones being adjusted to the following temperatures: 260° C., 270° C., 280° C. The extrudate is drawn through a water bath to cool it and then granulated. These granules are extruded a second and third time. The melt index is measured after these 3 extrusions (at 230° C. using 2.16 kg). A large increase in the melt index denotes marked chain degradation, i.e. poor stabilisation. The results are summarised in Table 3.

TABLE 3

| Compound from Example | Melt index |
|---|---|
| 1 | 4.9 |
| 2 | 5.5 |
| 3 | 9.3 |
| 5 | 6.7 |
| 6 | 11.1 |

TABLE 3-continued

| Compound from Example | Melt index |
|---|---|
| 7 | 8.7 |
| without additive | 16.5 |

EXAMPLE 15

Test for Retention of the Impact Strength of ABS (Acrylonitrile/Butadiene/Styrene Copolymer)

ABS (Terluran ® 996S, BASF) having a base stabilisation comprising 0.6% of 4,4'-thiobis(2-t-butyl-5-methylphenol), 0.1% of 1,1,3-tris(2'-methyl-4'-hydroxy-5'-t-butylphenyl)butane and 0.2% of dilauryl thiodipropionate is mixed with 0.15% of compound 1 (Table 1) and 0.3% of tris(2,4-di-t-butylphenyl)phosphite (=compound A). This mixture is extruded in a Plamver extruder at 100 rpm, the 3 heating zones being set to the following temperatures: 260° C., 270° C., 280° C. Sample articles are manufactured from the 1st, 3rd and 5th extrudate using an Aarburg injection-moulding machine (heating zone temperatures: 230° C./240° C./240° C., moulding temperature: 60° C., cycle duration: 35 seconds). These are tested in accordance with DIN 53753 for the retention of impact strength with the following results:

TABLE 4

| Stabiliser | Notch impact strength according to Charpy (DIN 53753) (KJ/m$^2$) | | |
|---|---|---|---|
| | 1x | 3x | 5x |
| — | 49 ± 6 | 36 ± 5 | 29 ± 5 |
| 0.15% of compound 1 + 0.3% of compound A | 57 ± 5 | 56 ± 5 | 51 ± 7 |

The results show that the notch impact strength is considerably better retained by the addition of the two additives.

EXAMPLE 16

Test for Stabilisation of Butadiene (BR) and Butadiene/Styrene Copolymer (SBS) During Brabender Processing Polybutadiene [BR BUNA CB HX 529C, comprising 0.3% of 2,6-di-tert-butyl-4-methylphenol (BHT) as base stabilisation] or butadiene/styrene copolymer [SBS Finapren 416, comprising BHT and trinonyl phosphite (TNPP) as base stabilisation] respectively are mixed with the processing stabiliser to be tested in the mixing chamber of a Brabender plastograph. The mixtures are kneaded at 60 rpm at the temperature indicated in Table 5 for 60 minutes. During this time, the kneading resistance is continuously recorded as the torque. Owing to the crosslinking of the polymer, a rapid increase in the torque occurs in the course of the kneading period after initial constancy. The activity of the stabilisers shows itself in a lengthening of the period of constancy. The values obtained can be taken from Table 5.

TABLE 5

| Compound from Table 1 | Amount added % | Butadiene 160° C. induction period [min] | SBS 200° C. induction period [min] |
|---|---|---|---|
| Reference | without additive | 9 | 7.5 |
| 1 | 0.25 | 23.5 | 40 |
| 1 + A* (mixture of 1 part of 1 and 2 parts of A) | 0.25 | 20 | 33 |
| 7 | 0.40 | — | 30.5 |

*A: Tri(2,4-di-tert-butylphenyl)phosphite

What is claimed is:

1. A stabilized composition comprising
(a) an organic material liable to thermal, oxidative and/or actinic degradation, which material is a lubricant, a metal processing fluid, a hydraulic fluid or a synthetic polymer, and
(b) an effective stabilizing amount of at least one compound of the formula (I)

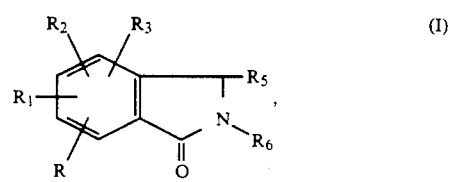

in which R is hydrogen, $C_1$-$C_{18}$alkyl, $C_1$-$C_{18}$alkoxy, halogen, nitro, phenyl-$C_1$-$C_4$alkoxy, $C_2$-$C_{18}$alkanoyl, benzoyl, ($C_1$-$C_6$alkyl)benzoyl, $C_2$-$C_{18}$alkenoyl, —N($R_7$)($R_{7a}$), —OH or —CO—A, $R_1$ has the same possibilities of meaning as R, $R_2$ is hydrogen or $C_1$-$C_4$alkyl and $R_3$ is hydrogen or halogen, A is hydroxyl, $C_1$-$C_{18}$alkoxy, $C_5$-$C_{12}$cycloalkoxy, benzyloxy or benzyloxy substituted by $C_1$-$C_4$alkyl and/or halogen, —N($R_7$)($R_{7a}$), —NH—NH—$R_8$ or —$G_1$—$(G)_n$, n is a number from 1 to 3 and G is a radical of the formula

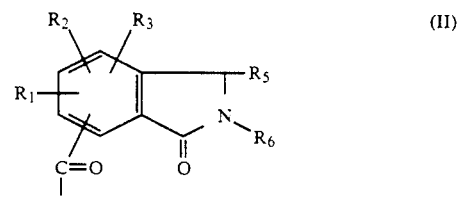

$G_1$ in the case where n=1 is —O—$R_{20}$—O—, —NH—$R_{21}$—NH— or —NH—NH—, in the case where n=2 is a group of the formula

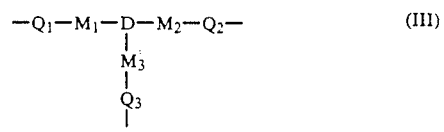

and in the case where n=3 is (—O—$CH_2$)$_4$C or

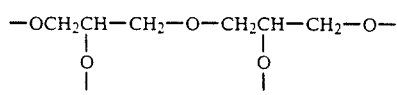

where D is N, CH or C($C_1$-$C_4$alkyl), $Q_1$, $Q_2$ and $Q_3$ independently of one another are O or NH and $M_1$, $M_2$ and $M_3$ independently of one another are $C_1-C_6$alkylene or $C_2-C_{12}$alkylene which is interrupted by —O—, or in the case where D=CH or $C(C_1-C_4alkyl)$ —$M_3$—$Q_3$ is also —O— or in the case where D=N —$M_3$—$Q_3$ is also a direct bond, $R_5$ and $R_6$ together form a group of the formula

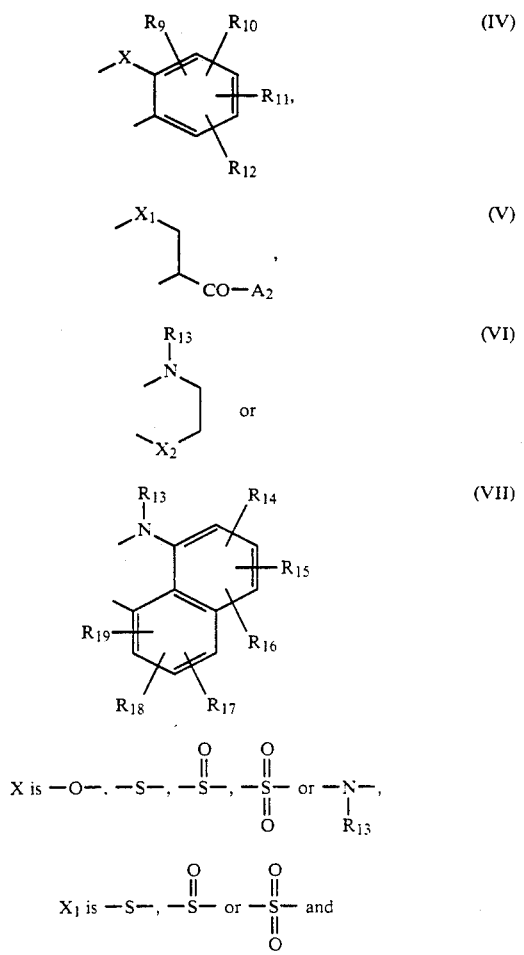

$X_2$ is —$CH_2$ or a direct bond, $R_7$ and $R_{7a}$ independently of one another are hydrogen, $C_1-C_{18}$alkyl, phenyl-$C_1-C_4$alkyl, $C_2-C_{18}$alkanoyl, $C_2-C_{18}$alkenoyl, $C_2-C_4$hydroxyalkyl, benzoyl or ($C_1-C_6$alkyl)-benzoyl or, together with the N atom to which they are bonded, are piperidyl, morpholinyl, piperazinyl or 4-methylpiperazinyl, $R_8$ is hydrogen, $C_2-C_{18}$alkanoyl, benzoyl or ($C_1-C_6$alkyl)benzoyl, $R_9$, $R_{10}$, $R_{11}$ and $R_{12}$ have the same possibilities of meaning as R, $R_1$, $R_2$ and $R_3$ (in this sequence), where —CO—A is to be replaced by —CO—$A_1$, $R_{13}$ is hydrogen, $C_1-C_{18}$alkyl, $C_2-C_{18}$alkenyl, $C_5-C_{12}$cycloalkyl, phenyl-$C_1-C_4$alkyl, $C_2-C_{18}$alkanoyl, $C_2-C_{18}$alkenoyl, benzoyl, ($C_1-C_6$alkyl)-benzoyl, cyano-$C_1-C_4$alkyl, $C_2-C_{19}$alkoxycarbonyl-$C_1-C_4$alkyl, carboxy-$C_1-C_4$alkyl, hydroxy-$C_1-C_4$alkyl or

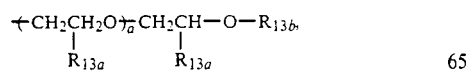

$R_{13a}$ is hydrogen or methyl and $R_{13b}$ is hydrogen, $C_1-C_{18}$alkyl, phenyl-$C_1-C_4$alkyl, $C_1-C_{18}$alkanoyl, benzoyl, $C_2-C_{18}$alkenoyl or ($C_1-C_6$alkyl)benzoyl and a is a number from 0 to 6, $R_{14}$, $R_{15}$, $R_{16}$, $R_{17}$, $R_{18}$ and $R_{19}$ independently of one another are hydrogen, $C_1-C_4$alkyl, halogen, hydroxyl, $C_1-C_{18}$alkoxy or —$N(R_{7b})(R_{7c})$, in which $R_{7b}$ and $R_{7c}$ independently of one another are hydrogen or $C_1-C_{18}$alkyl, $R_{20}$ is $C_1-C_{12}$alkylene, $C_2-C_8$alkenylene, $C_3-C_6$alkynylene or $C_2-C_{24}$alkylene which is interrupted by O, S and/or —$N(R_{22})$—, $R_{21}$ is $C_1-C_{12}$alkylene and $R_{22}$ is hydrogen, $C_1-C_{18}$alkyl, phenyl, ($C_1-C_6$alkyl)phenyl or phenyl-$C_1-C_4$alkyl, $A_1$ is hydroxyl, $C_1-C_{24}$alkoxy, $C_5-C_{12}$cycloalkoxy, benzyloxy or benzyloxy substituted by $C_1-C_6$alkyl and/or halogen, —$N(R_7)(R_{7a})$, —NH—NH—$R_8$ or —$G_1$—$(G_2)_n$, and $A_2$ is hydroxyl, $C_1-C_{24}$alkoxy, $C_5-C_{12}$cycloalkoxy, benzyloxy or benzyloxy substituted by $C_1-C_6$alkyl and/or halogen, —$N(R_7)(R_{7a})$, —NH—NH—$R_8$ or —$G_1$—$(G_3)_n$, where $G_1$ and n are as defined above, $G_2$ is a radical of the formula

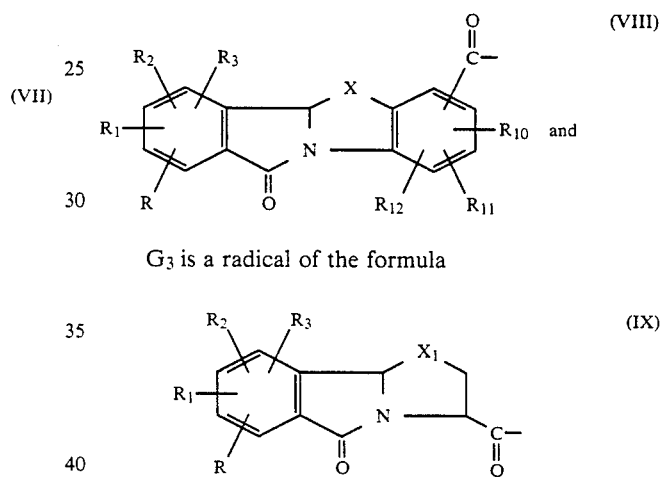

$G_3$ is a radical of the formula

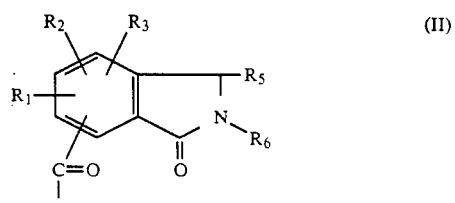

with the proviso that only one substituent —CO—A, CO—$A_1$ or —CO—$A_2$ is present in the molecule, in which A, $A_1$ or $A_2$ is a radical —$G_1$—$(G)_n$, —$G_1$—$(G_2)_n$ or —$G_1$—$(G_3)_n$; with the further proviso that silver halide containing photographic emulsions are excluded from the organic material of component (a).

2. A composition according to claim 1, in which R is hydrogen, hydroxyl, $C_1-C_4$alkyl, chlorine, nitro, $C_1-C_4$alkoxy, benzoyl, -$N(R_7)(R_{7a})$ or —CO—A, $R_1$ has the same possibilities of meaning as R, $R_2$ is hydrogen or $C_1-C_3$alkyl and $R_3$ is hydrogen or chlorine, A is hydroxyl, $C_1-C_{18}$alkoxy, $C_5-C_6$cycloalkoxy, benzyloxy or benzyloxy substituted by $C_1-C_4$alkyl and/or chlorine, —$N(R_7)(R_{7a})$ or —$G_1$—$(G)_n$, n is a number from 1 to 3 and G is a radical of the formula $G_1$ in the case where n=1 is $-O-R_{20}-O-$ or $-NH-R_{21}-NH-$, in the case where n=2 is a group of the formula

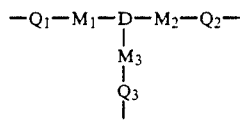 (III)

and in the case where n=3 is $(-OCH_2)_4C$, where D is equal to N, CH or $C(C_1-C_4alkyl)$, $Q_1$, $Q_2$ and $Q_3$ independently of one another are O or NH and $M_1$, $M_2$ and $M_3$ independently of one another are $C_1-C_6alkylene$ or $C_2-C_{12}alkylene$ interrupted by $-O-$, or in the case where D=CH or $C(C_1-C_4alkyl)$ $-M_3-Q_3$ is also $-O-$ or in the case where D=N $-M_3-Q_3$ is also a direct bond, $R_5$ and $R_6$ together from a group of the formula IV, V, VI or VII, $R_7$ and $R_{7a}$ independently of one another are hydrogen, $C_1-C_6alkyl$, benzyl, $C_2-C_4$-hydroxyalkyl or, together with the N atom to which they are bonded, are piperidyl, morpholinyl, piperazinyl or 4-methylpiperazinyl, $R_9$, $R_{10}$, $R_{11}$ and $R_{12}$ have the same possibilities of meaning as R, $R_1$, $R_2$ and $R_3$ (in this sequence), where $-CO-A$ is to be replaced by $-CO-A_1$, $R_{13}$ is hydrogen, $C_1-C_{18}alkyl$, $C_2-C_{18}alkenyl$, $C_5-C_6cycloalkyl$, phenyl-$C_1-C_4alkyl$, $C_2-C_{18}alkenoyl$, $C_2-C_{18}alkenoyl$, benzoyl, $(C_1-C_6alkyl)benzoyl$, cyano-$C_1-C_4alkyl$, $C_2-C_{19}alkoxycarbonyl-C_1-C_4alkyl$, carboxy-$C_1-C_4alkyl$ or hydroxy-$C_2-C_4alkyl$, $R_{14}$, $R_{15}$, $R_{16}$, $R_{17}$, $R_{18}$ and $R_{19}$ independently of one another are hydrogen, $C_1-C_4alkyl$, chlorine, hydroxyl, $C_1-C_4alkoxy$ or $-N(R_{7b})(R_{7c})$, in which $R_{7b}$ and $R_{7c}$ independently of one another are hydrogen or $C_1-C_6alkyl$, $R_{20}$ is $C_1-C_{12}alkylene$, $C_2-C_8alkenylene$, $C_3-C_6alkynylene$ or $C_2-C_{24}alkylene$ interrupted by O, S and/or $-N(R_{22})$, $R_{21}$ is $C_1-C_{12}alkylene$ and $R_{22}$ is hydrogen or $C_1-C_4alkyl$, $A_1$ is hydroxyl, $C_1-C_{18}alkoxy$, $C_5-C_6cycloalkoxy$, benzyloxy or benzyloxy substituted by $C_1-C_4alkyl$ and/or halogen, $-N(R_7)(R_{7a})$ or $-G_1-(G_2)_n$ and $A_2$ is hydroxyl, $C_1-C_{18}alkoxy$, $C_5-C_6cycloalkoxy$, benzyloxy or benzyloxy substituted by $C_1-C_4alkyl$ and/or halogen, $-N(R_7)(R_{7a})$ or $-G_1-(G_3)_n$, where $G_1$ and n are as defined above, $G_2$ is a radical of the formula

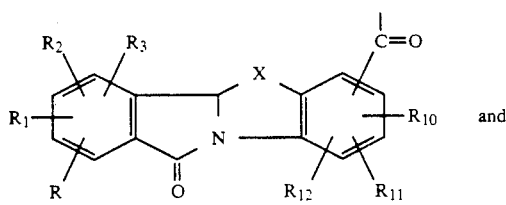 and $G_3$ is a radical of the formula

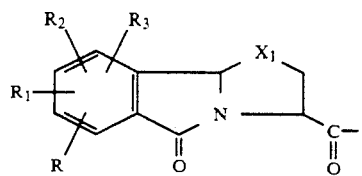

3. A composition according to claim 1, in which R is hydrogen, chlorine, hydroxyl or $C_1-C_4alkyl$, $R_1$ is hydrogen, chlorine, $C_1-C_4alkyl$ or hydroxyl, $R_2$ and $R_3$ are hydrogen, $R_5$ and $R_6$ together form a group of the formula IV, V, VI or VII, $R_9$, $R_{10}$, $R_{11}$ and $R_{12}$ have the same possibilities of meaning as R, $R_1$, $R_2$ and $R_3$ (in this sequence), $R_{13}$ is hydrogen, $C_1-C_{18}alkyl$, $C_5-C_6cycloalkyl$, benzyl, $C_2-C_{19}alkoxycarbonyl-C_1-C_4alkyl$, carboxy-$C_1-C_4alkyl$, $C_2-C_{18}alkanoyl$ or benzoyl, $R_{14}$, $R_{15}$, $R_{16}$, $R_{17}$, $R_{18}$ and $R_{19}$ are hydrogen and $A_2$ is hydroxyl, $C_1-C_{18}alkoxy$, $C_5-C_6cycloalkoxy$ or benzyloxy.

4. A composition according to claim 1, in which R and $R_9$ independently of one another are hydrogen, $C_1-C_4alkyl$ or chlorine and $R_1$, $R_2$, $R_3$, $R_{10}$, $R_{11}$, $R_{12}$, $R_{14}$, $R_{15}$, $R_{16}$, $R_{17}$, $R_{18}$ and $R_{19}$ are hydrogen.

5. A composition according to claim 1, in which A, $A_1$ and $A_2$ are different from $-G_1-(G)_n$, $-G_1-(G_2)_n$ or $-G_1-(G_3)_n$.

6. A composition according to claim 1, in which R is hydrogen, methyl or chlorine, $R_1$, $R_2$ and $R_3$ are hydrogen, and $R_5$ and $R_6$ together are a group of the formula IV, V, VI or VII in which X is $-S-$,

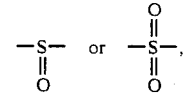

$X_1$ is $-S-$, $X_2$ is $-CH_2-$, $R_9$ is hydrogen, $-CH_3$, Cl or $-COO-(C_1-C_{24}alkyl)$, $R_{10}$, $R_{11}$ and $R_{12}$ are hydrogen, $R_{13}$ is hydrogen, $C_1-C_{18}alkyl$, benzoyl, $C_2-C_{19}alkoxycarbonyl-C_1-C_4methyl$ or $C_2-C_{18}alkanoyl$, $R_{14}$ to $R_{19}$ are hydrogen and $A_2$ is $C_1-C_{24}alkoxy$.

7. A composition according to claim 1, in which the organic material is a lubricant.

8. A composition according to claim 1, in which the organic material is a thermoplastic or an elastomer.

9. A composition according to claim 8, in which the organic material is a polyolefin.

10. A composition according to claim 1, which additionally contains other stabilisers such as antioxidants, light stabilisers and processing stabilisers (heat stabilisers).

11. A composition according to claim 10, which contains at least one organic phosphite or phosphonite.

12. A process for stabilizing an organic material, subject to thermal, oxidative or actinic degradation, which comprises
adding to said organic material an effective stabilizing amount of a compound of formula I according to claim 1.

13. A process according to claim 12 for stabilising lubricants, metal processing fluids and hydraulic fluids and natural, synthetic or semisynthetic polymers.

* * * * *